United States Patent [19]

Zimmerman et al.

[11] Patent Number: 6,147,188
[45] Date of Patent: *Nov. 14, 2000

[54] α- (1,3- OR 1, 2- DICARBONYLENOL ETHER METHYL KETONES AS CYSTEINE PROTEASE INHIBITORS

[75] Inventors: Mary P. Zimmerman, Pleasonton; Robert E. Smith, Livermore; Mark Becker, Walnut Creek, all of Calif.

[73] Assignee: Prototek, Inc., Dublin, Calif.

[*] Notice: This patent is subject to a terminal disclaimer.

[21] Appl. No.: 09/017,276

[22] Filed: Feb. 2, 1998

Related U.S. Application Data

[63] Continuation of application No. 08/481,808, Jun. 7, 1995, Pat. No. 5,714,484, which is a continuation-in-part of application No. 08/164,031, Dec. 8, 1993, Pat. No. 5,486,623.

[51] Int. Cl.$^7$ .............................. C07K 5/00; C07K 7/00
[52] U.S. Cl. .................. 530/330; 514/430; 514/438; 514/461; 514/441; 549/29; 549/62
[58] Field of Search ..................................... 530/330, 331; 514/430, 438, 461, 441; 549/29, 62

[56] References Cited

U.S. PATENT DOCUMENTS

| | | | |
|---|---|---|---|
| 4,518,528 | 5/1985 | Rasnick | 260/112.5 |
| 4,959,503 | 9/1990 | Connor et al. | 564/265 |
| 5,055,451 | 10/1991 | Krantz et al. | 514/19 |
| 5,158,936 | 10/1992 | Krantz et al. | 514/19 |
| 5,283,158 | 2/1994 | Onodera et al. | 430/264 |
| 5,462,939 | 10/1995 | Dolle et al. | 514/231.5 |
| 5,486,623 | 1/1996 | Zimmerman et al. | 549/417 |
| 5,498,616 | 3/1996 | Mallamo et al. | 514/300 |
| 5,585,486 | 12/1996 | Dolle et al. | 544/182 |
| 5,663,380 | 9/1997 | Zimmerman et al. | 549/477 |
| 5,714,484 | 2/1998 | Zimmerman et al. | 514/231.5 |

FOREIGN PATENT DOCUMENTS

| | | |
|---|---|---|
| 0 272 671 | 6/1988 | European Pat. Off. . |
| 0 525 420 A1 | 2/1993 | European Pat. Off. . |
| 0 623 592 A1 | 4/1994 | European Pat. Off. . |
| 0 644 198 A1 | 3/1995 | European Pat. Off. . |
| 62754 | 5/1993 | United Kingdom . |
| WO93/09135 | 5/1993 | WIPO . |
| WO 95/26958 | 12/1995 | WIPO . |
| WO 96/03982 | 2/1996 | WIPO . |

OTHER PUBLICATIONS

Chemical Abstract 120:135102 (1993).
Chemical Abstract 113:2570 (1989).
Chemical Abstract 78:43256 (1972).

*Primary Examiner*—Marianne M. Cintins
*Assistant Examiner*—C. Delacroix-Muirhei
*Attorney, Agent, or Firm*—Woodard, Emhardt, Naughton, Moriarty & McNett

[57] ABSTRACT

Cysteine protease inhibitors which deactivate the protease by covalently bonding to the cysteine protease and releasing the enolate of a 1,3-dicarbonyl (or its enolic form). The cysteine protease inhibitors of the present invention accordingly comprise a first portion which targets a desired cysteine protease and positions the inhibitor near the thiolate anion portion of the active site of the protease, and a second portion which covalently bonds to the cysteine protease and irreversibly deactivates that protease by providing a carbonyl or carbonyl-equivalent which is attacked by the thiolate anion of the active site of the cysteine protease to sequentially cleave a β-dicarbonyl enol ether leaving group.

4 Claims, No Drawings"

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Binding Site for Interleukin
      1-Beta - Converting Enzyme

<400> SEQUENCE: 1

Tyr Val Ala Asp

α- (1,3- OR 1, 2- DICARBONYLENOL ETHER METHYL KETONES AS CYSTEINE PROTEASE INHIBITORS

This application is a continuation of applicants' application Ser. No. 08/481,808, filed Jun. 7, 1995, now U.S. Pat. No. 5,714,484, which is a continuation-in-part of Ser. No. 08/164,031, filed Dec. 8, 1993, now U.S. Pat. No. 5,486,623.

FIELD OF THE INVENTION

The present invention relates generally to cysteine protease inhibitors, and more particularly to cysteine protease inhibitors which are peptidyl ketones which contain dicarbonyl enolether leaving groups. The cysteine protease inhibitors of the present invention are particularly designed for the in vivo management of cysteine proteases, particularly cathepsins B, L, H and C, calpains I and II, interkeukin 1-β-conveting enzyme ("ICE"), and the primitive enzymatic counterparts of these cysteine proteases.

BACKGROUND TO THE INVENTION

Cysteine proteases associated with human disease states can be grouped into three categories: (1) lysosomal cathepsins; (2) cytosolic calpains and processing enzymes such as interkeukin conveting enzymes; and (3) prokaryotic enzymes with autocatalytic activation. Cathepsins B, H, and L are cysteinyl proteases involved in normal protein degradation. As such, they are generally located in the lysosomes of cells. When these enzymes are found extralysosomaly they have been implicated by use of synthetic substrate technology and by natural endogenous inhibitors as playing a causative role in a number of disease states such as rheumatoid arthritis, osteo arthritis, pneumocystis carinii, schistosomiasis, trypanosoma cruzi, trypanosoma brucei brucei, *Crithidia fusiculata,* malaria, periodontal disease, tumor metastasis, metachromatic leukodystrophy, muscular dystrophy, etc. For example, a connection between cathepsin B-type enzymes and rheumatoid arthritis has been suggested in van Noorden and Everts, "Selective Inhibition of Cysteine Proteinases by Z-Phe-Ala-CH$_2$F Suppresses Digestion of Collagen by Fibroblasts and Osteoclasts," 178 *Biochemical and Biophysical Research Communications* 178; Rifkin, Vernillo, Kleekner, Auszmann, Rosenberg and Zimmerman, "Cathepsin B and L Activities in Isolated Osteoclasts," 179 *Biochemical and Biophysical Research Communications* 63; Grinde, "The Thiol Proteinase Inhibitors, Z-Phe-Phe-CHN$_2$ and Z-Phe-Ala-CHN$_2$, Inhibit Lysosomal Protein Degradation in Isolated Rat Hepatocytes," 757 *Biochimica et Biophysica Acta* 15; Mason, Bartholomew and Hardwick, "The Use of Benzyloxycarbonyl[$^{125}$I] iodotyrosylalanyldiazomethane as a Probe for Active Cysteine Proteinases in Human Tissues," 263 *Biochem. J.* 945; van Noorden, Smith and Rasnick, "Cysteine Proteinase Activity in Arthritic Rat Knee Joints and the Effects of a Selective Systemic Inhibitor, Z-Phe-Ala-CH$_2$F," 15 *J. Rheumatol.* 1525; and van Noorden, Vogels and Smith, "Localization and Cytophotometric Analysis of Cathepsin B Activity in Unfixed and Undecalified Cryostat Sections of Whole Rat Knee Joints," 37 *J. Histochemistry and Cytochemistry* 617. A connection between cathepsin B and osteo arthritis has been suggested in Delaissé, Eeckhout and Vaes, "In Vivo and In Vitro Evidence for the Involvement of Cysteine Proteinases in Bone Resorption," 125 *Biochemical and Biophysical Research Communications* 441; a connection between cathepsin B and pneumocystis carinii has been suggested in Hayes, Stubberfield, McBride and Wilson, "Alterations in Cysteine Proteinase Content of Rat Lung Associated with Development of Pneumocystis Carinii Infection," 59 *Infection and Immunity* 3581; a connection between cysteine proteinases and schistosomiasis has been suggested in Cohen, Gregoret, Amiri, Aldape, Railey and McKerrow, "Arresting Tissue Invasion of a Parasite by Protease Inhibitors Chosen With the Aid of Computer Modeling," 30 *Biochemistry* 11221. A connection between cysteine proteinases and trypanosoma cruzi, trypanosoma brucei brucei and crithidia fasciculata has been suggested in Ashall, Harris, Roberts, Healy and Shaw, "Substrate Specificity and Inhibitor Sensitivity of a Trypanosomatid Alkaline Peptidase," 1035 *Biochimica et Biophysica Acta* 293, and/or in Ashall, Angliker and Shaw, "Lysis of Trypanosomes by Peptidyl Fluoromethyl Ketones," 170 *Biochemical and Biophysical Research Communications* 923. A connection between cysteine proteinases and malaria has been suggested in Rosenthal, Wollish, Palmer and Rasnick, "Antimalarial Effects of Peptide Inhibitors of a Plasmodium Falciparum Cysteine Proteinase," 88 *J. Clin. Invest.* 1467, and in Rosenthal, Lee and Smith, "Inhibition of a Plasmodium Vinckei Cysteine Proteinase Cures Murine Malaria," 91 *J. Clin. Invest.* 1052. A connection between cathepsin B and tumor metathesis has been suggested in Smith, Rasnick, Burdick, Cho, Rose and Vahratian, "Visualization of Time-Dependent Inactivation of Human Tumor Cathepsin B Isozymes by a Peptidyl Fluoromethyl Ketone Using a Fluorescent Print Technique," 8 *Anti-cancer Research* 525. A connection between cathepsin B and cancer has been suggested in Gordon and Mourad, 2 *Blood Coagulation and Fibrinolysis* 735. A connection between cathepsin B and periodontal disease has been suggested in Cox, Cho, Eley and Smith, "A Simple, Combined Fluorogenic and Chromogenic Method for the Assay of Proteases in Gingival Crevicular Fluid," 25 *J. Periodont. Res.* 164; Uitto, Larjava, Heino and Sorsa, "A Protease of Bacteroides Gingivalis Degrades Cell Surface and Matrix Glycoproteins of Cultured Gingival Fibroblasts and Induces Secretion of Collagenase and Plasminogen Activator," 57 *Infection and Immunity* 213; Kunimatsu, Yamamoto, Ichimaru, Kato and Kato, "Cathepsins B, H and L Activities in Gingival Crevicular Fluid From Chronic Adult Periodontitis Patients and Experimental Gingivitis Subjects," 25 *J Periodont Res* 69; Beighton, Radford and Naylor, "Protease Activity in Gingival Crevicular Fluid From Discrete Periodontal Sites in Humans With Periodontitis or Gingivitis"; 35 *Archs oral Biol.* 329; Cox and Eley, "Preliminary Studies on Cysteine and Serine Proteinase Activities in Inflamed Human Gingiva Using Different 7-Amino-4-Trifluoromethyl Coumarin Substrates and Protease Inhibitors," 32 *Archs oral Biol.* 599; and Eisenhauer, Hutchinson, Javed and McDonald, "Identification of a Cathepsin B-Like Protease in the Crevicular Fluid of Gingivitis Patients," 62 *J Dent Res* 917. A connection between cathepsin B and metachromatic leukodystrophy has been suggested in von Figura, Steckel, Conary, Hasilik and Shaw, "Heterogeneity in Late-Onset Metachromatic Leukodystrophy. Effect of Inhibitors of Cysteine Proteinases," 39 *Am J Hum Genet.* 371; a connection between cathepsin B and muscular leukodystrophy has been suggested in Valentine, Winand, Pradhan, Moise, de Lahunta, Kornegay and Cooper, "Canine X-Linked Muscular Dystrophy as an Animal Model of Duchenne Muscular Dystrophy: A Review," 42 *Am J Hum Genet* 352; a connection between cathepsin B and rhinovirus has been suggested in Knott, Orr, Montgomery, Sullivan and Weston, "The Expression and Purification of Human Rhinovirus Protease 3C," 182 *Eur. J. Biochem.* 547; a connection between cathepsin B and kidney disease has been suggested in Baricos, O'Connor, Cortez, Wu and Shah, "The Cysteine Proteinase Inhibitor, E-64, Reduces Proteinuria in an Experimental Model of Glomerulonephritis," 155 *Biochemical and Biophysical Research Communications* 1318; and a connection between cathepsin B and multiple sclerosis has been suggested in Dahlman, Rutschmann, Kuehn and Reinauer, "Activation of the Multicatalytic Proteinase from Rat Skeletal Muscle by Fatty Acids or Sodium Dodecyl Sulphate," 228 *Biochem. J.* 171.

Connections between certain disease states and cathepsins H and C have also been established. For example, cathepsin H has been directly linked to the causative agents of Pneumocystis carinii and in the neuromuscular diseases Duchenne dystrophy, polymyositis, and neurogenic disorders. Stauber, Riggs and Schochet, "Fluorescent Protease Histochemistry in Neuromuscular Disease," *Neurology* 194 (Suppl. 1) March 1984; Stauber, Schochet, Riggs, Gutmann and Crosby, "Nemaline Rod Myopathy: Evidence for a Protease Deficiency," *Neurology* 34 (Suppl. 1) March 1984. Similarly, cathepsin C has been directly linked to muscular diseases such as nemaline myopathy, to viral infections, and to processing and activation of bone marrow serine proteases (elastase and granzyme A). McGuire, Lipsky and Thiele, "Generation of Active Myeloid and Lymphod Granule Serine Proteases Requires Processing by the Granule Thiol Protease Dipeptidyl Peptidase I, 268 *J. Biol. Chem.* 2458–67; L. Polgar, Mechanisms of Protease Action (1989); Brown, McGuire and Thiele, "Dipeptidyl Peptidase I is Enriched in Granules of In Vitro- and In Vivo-Activated Cytotoxic T Lymphocytes," 150 *Immunology* 4733–42. The Brown et al. study effectively demonstrated the feasibility of inhibiting cathepsin C (DPP-I) in the presence of other cysteinyl enzymes based on substrate specificity. Unfortunately, the diazoketones used in that study are believed to be mutagenic and not appropriate for in vivo application.

The cytosolic or membrane-bound cysteine proteases called calpains have also been implicated in a number of disease states. For example, calpain inhibitor can be useful for the treatment of muscular disease such as muscular dystrophy, amyotrophy or the like, 25 Taisha (Metabolism) 183 (1988); 10 *J. Pharm. Dynamics* 678 (1987); for the treatment of ischemic diseases such as cardiac infarction, stroke and the like, 312 *New Eng. J. Med.* 159 (1985); 43 Salshin Igaku 783 (1988); 36 *Arzneimittel Forschung/Drug Research* 190, 671 (1986); 526 *Brain Research* 177 (1990); for improving the consciousness disturbance or motor disturbance caused by brain trauma, 16 *Neurochemical Research* 483 (1991); 65 *J. Neurosurgery* 92 (1986); for the treatment of diseases caused by the demyelination of neurocytes such as multiple sclerosis, peripheral nervous neuropathy and the like, 47 *J. Neurochemistry* 1007 (1986); and for the treatment of cataracts, 28 *Investigative Ophthalmology & Visual Science* 1702 (1987); 34 *Experimental Eye Research* 413 (1982); 6 *Lens and Eye Toxicity Research* 725 (1989): 32 *Investigative Ophthalmology & Visual Science* 533 (1991).

Calpain inhibitors may also be used as therapeutic agents for fulminant hepatitis, as inhibitors against aggregation of platelet caused by thrombin, 57 *Thrombosis Research* 847 (1990); and as a therapeutic agent for diseases such as breast carcinoma, prostatic carcinoma or prostatomegaly, which are suspected of being caused by an abnormal activation of the sex hormone receptors.

Certain protease inhibitors have also been associated with Alzheimer's disease. See, e.g., 11 *Scientific American* 40 (1991). Further, thiol protease inhibitors are believed to be useful as anti-inflammatory drugs, 263 *J. Biological Chem.* 1915 (1988); 98 *J. Biochem.* 87 (1985); as antiallergic drugs, 42 *J. Antibiotics* 1362 (1989); and to prevent the metastasis of cancer, 57 *Seikagaku* 1202 (1985); *Tumor Progression and Markers* 47 (1982); and 256 *J. Biological Chemistry* 8536 (1984).

Further, Interleukin 1-β-Converting Enzyme (ICE) has been shown to be a cysteine protease implicated in the formation of the cytokine IL-1β which is a potent mediator in the pathogenesis of chronic and acute inflammatory diseases. Tocci and Schmidt, *ICOP Newsletter*, September 1994. Inhibitors to this enzyme have recently been reported, including Thornberry, Peterson, Zhao, Howard, Griffin, and Chapman, Inactivation of Interleukin-1β-Converting Enzyme by Peptide (Acyloxy)methyl Ketones, 33 *Biochemistry* 3934 (1994); Dolle, Singh, Rinker, Hoyer, Prasad, Graybill, Salvino, Helaszek, Miller and Ator, "Aspartyl α-((1-Phenyl-3-(trifluoromethyl)-pyrazol-5-yl)oxy)methyl Ketones as Interleukin-1β Converting Enzyme Inhibitors: Significance of the $P_1$ and $P_3$ Amido Nitrogens for Enzyme-Peptide Inhibitor Binding" 37 *J. Med. Chem.* 3863; Mjalli, Chapman, MacCoss, Thornberry, Peterson, Activated Ketones as Potent Reversible Inhibitors of Interleukin-1β-Converting Enzyme" 4 *Biooganic & Medicinal Chemistry Letters,* 1965; and Dolle, Singh, Whipple, Osifo, Speier, Graybill, Gregory, Harris, Helaszek, Miller and Ator "Aspartyl α-((Diphenylphosphinyl)-oxy)-methyl Ketones as Novel Inhibitors of Interleukin-1β-Converting Enzyme: Utility of the Diphenylphosphionic Acid Leaving Group for the Inhibition of Cysteine Proteases" 38 *J. Med Chem.* 220.

The most promising type of cysteine proteinase inhibitors have an activated carbonyl with a suitable α-leaving group fused to a programmed peptide sequence that specifically directs the inhibitor to the active site of the targeted enzyme. Once inside the active site, the inhibitor carbonyl is attacked by a cysteine thiolate anion to give the resulting hemiacetal, which collapses via a 1,2-thermal migration of the thiolate and subsequent displacement of the α-keto-leaving group. The bond between enzyme and inhibitor is then permanent and the enzyme is irreversibly inactivated.

The usefulness of an inhibitor in inactivating a particular enzyme therefore depends not only on the "lock and key" fit of the peptide portion, but also on the reactivity of the bond holding the α-leaving group to the rest of the inhibitor. It is important that the leaving group be reactive only to the intramolecular displacement via a 1,2-migration of sulfur in the breakdown of the hemithioacetal intermediate.

Groundbreaking work regarding cysteine proteinase inhibitors having an activated carbonyl, a suitable α-leaving group and a peptide sequence that effectively and specifically directs the inhibitor to the active site of the targeted enzyme was disclosed in U.S. Pat. No. 4,518,528 to Rasnick, incorporated herein by reference. That patent established peptidyl fluoromethyl ketones to be unprecedented inhibitors of cysteine proteinase in selectivity and effectiveness. The fluoromethyl ketones described and synthesized by Rasnick included those of the formula:

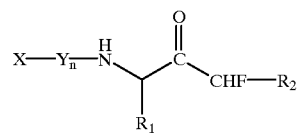

wherein $R_1$ and $R_2$ are independently selected from the group hydrogen, alkyl of 1–6 carbons, substituted alkyl of 1–6 carbons, aryl, and alkylaryl where the alkyl group is of 1–4 carbons; n is an integer from 1–4 inclusive; X is a peptide end-blocking group; and Y is an amino acid or peptide chain of from 1–6 amino acids.

Peptidylketone inhibitors using a phenol leaving group are similar to the peptidyl fluoroketones. As is known in the art, oxygen most closely approaches fluorine in size and electronegativity. Further, when oxygen is bonded to an aromatic ring these values of electronegativity become even closer due to the electron withdrawing effect of the $sp^2$ carbons. The inductive effect of an α-ketophenol versus an α-ketofluoride when measured by the pKa of the α-hydrogen, appears comparable within experimental error.

Unfortunately, the leaving groups of prior art inhibitors that use a phenoxy group present problems of toxicity, solubility, etc. Solubility is of particular importance in the field of peptide derived drugs where bioavailability becomes the major criterion for the success of a drug. The solubility recommendation of the FDA is 5 mg/mL. Successful in vivo utility of prior art inhibitors has been limited due to the insolubility of the leaving groups. In vivo application to date has centered on inhibitors with peptide requirements allowing ester, acid or free amine side chains as those required in the inhibition of Interleukin-1β-converting enzyme: Revesz, Briswalter, Heng, Leutwiler, Mueller and Wuethrich, "35 *Tetrahedron Letters* 9693.

International application WO 93/09135 disclosed inhibitors again designed for Interleukin-1β-converting enzyme where an N-hydroxytetrazole was disclosed as a leaving group. Further, tetrazoles have also been used in other pharmaceutical products such as Ceforanide, etc.

The in vivo inhibition of other cysteine proteases using oxygen anionic leaving groups was first disclosed by Zimmerman, Bissell, and Smith in U.S. Pat. No. 5,374,623 where it was disclosed that bioavailability is enhanced by the use of peptidyl α-aromatic ether methyl ketones with selective peptide combinations not requiring the presence of a free amine or acid side chain. Later, a peptidyl (acyloxy) methyl ketone with lysine in the side chain was reported to have in vivo efficacy: Wagner, Smith, Coles, Copp, Ernest and Krantz, "In Vivo Inhibition of Cathepsin B by Peptidyl (Acyloxy)methyl Ketones," 37 *J. Med. Chem.* 1833. Unfortunately, peptidyl (acyloxy)methyl ketones are esters that are also subject to cleavage by esterases which makes the α-ketoethers the preferred construction for cysteine protease inhibitors.

It can be seen from the foregoing that a need continues to exist for cysteine protease inhibitors with improved solubility and toxicity profiles, and which are particularly suitable for in vivo use. The present invention addresses that need.

SUMMARY OF THE INVENTION

Briefly describing the present invention, there is provided a class of cysteine protease inhibitors which deactivates the protease by covalently bonding to the cysteine protease and releasing the enolate of a 1,3-dicarbonyl (or its enolic form). The cysteine protease inhibitors of the present invention accordingly comprise a first portion which targets a desired cysteine protease and positions the inhibitor near the thiolate anion portion of the active site of the protease, and a second portion which covalently bonds to the cysteine protease and irreversibly deactivates that protease by providing a carbonyl or carbonyl-equivalent which is attacked by the thiolate anion of the active site of the cysteine protease to sequentially cleave a β-dicarbonyl enol ether leaving group.

The cysteine protease inhibitors of the present invention may be defined by the formula below:

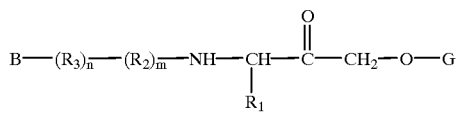

where

B is H or an N-terminal blocking group;

$R_{1-3}$ are the amino acid side chains of the $P_{1-3}$ amino acids, respectively;

n is 0 or 1;

m is 0 or 1; and

G is a five- or six-membered ring portion of the β-dicarbonyl enol ether leaving group as defined by the formulas below.

In one embodiment, the compositions of the present invention are cathepsin or calpain inhibitors of the formula:

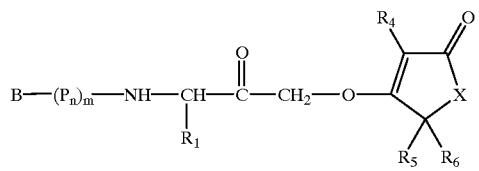

where

B is H or an N-terminal blocking group;

$R_1$ is the amino acid side chain of the $P_1$ amino acid residue; wherein the $P_1$ amino acid is not Asp;

each $P_n$ is an amino acid residue, or is a heterocyclic replacement of the amino acid wherein the heterocycle is a piperazine, a decahydroisoquinoline, a pyrrolinone, a pyridine, a pyridone, a carbolinone, a quinazoline, a pyrimidone or the like;

m is 0 or a positive integer;

$R_4$ is a hydroxyl, alkoxyl, acyl, hydrogen, alkyl or phenyl;

$R_5$ and $R_6$ are jointly a carboxyl group or a double bond terminating in an alkyl or an aryl group, or are independently acyl, aryl or heteroaryl if $R_4$ is hydrogen, alkyl or phenyl, or are independently acyl, alkyl, hydrogen, aryl or heteroaryl otherwise; and X is N, S, O or $CH_2$.

In another embodiment, the compositions of the present invention are ICE inhibitors of the formula:

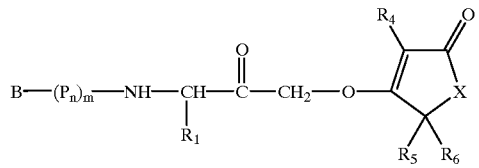

where

B is H or an N-terminal blocking group;

$R_1$ is the Asp amino acid side chain;

each $P_n$ is an amino acid residue, or is a heterocyclic replacement of the amino acid wherein the heterocycle is a piperazine, a decahydroisoquinoline, a pyrrolinone, a pyridine, a pyridone, a carbolinone, a quinazoline, a pyrimidone or the like;

m is 0 or a positive integer;

$R_4$ is a hydroxyl, alkoxyl, acyl, hydrogen, alkyl or phenyl;

$R_5$ and $R_6$ are jointly a carboxyl group or a double bond terminating in an alkyl or an aryl group, or are independently acyl, aryl or heteroaryl if $R_4$ is hydrogen, alkyl or phenyl, or are independently acyl, alkyl, hydrogen, aryl or heteroaryl otherwise; and X is N, S, O or $CH_2$.

In another embodiment, the cysteine protease inhibitor is of the formula:

$$B\text{—}(P_n)_{\overline{m}}\text{—}NH\text{—}\underset{R_1}{CH}\text{—}\underset{\parallel}{\overset{O}{C}}\text{—}CH_2\text{—}O\diagdown\diagup\underset{R_{10}}{\diagdown}X\diagdown O$$

where

B is H or an N-terminal blocking group;

each $P_n$ is an amino acid residue, or is a heterocyclic replacement of the amino acid wherein the heterocycle is a piperazine, a decahydroisoquinoline, a pyrrolinone, a pyridine, a pyridone, a carbolinone, a quinazoline, a pyrimidone or the like;

m is 0 or a positive integer;

$R_4$ is a hydroxyl, alkoxyl, acyl, hydrogen, alkyl or phenyl;

$R_{10}$ is H or an optionally substituted alkyl, aryl, heteroaryl, or the residue of a sugar; and X is N, S, O or $CH_2$.

In another embodiment, the cysteine protease inhibitor is of the formula:

$$B\text{—}(P_n)_{\overline{m}}\text{—}NH\text{—}\underset{R_1}{CH}\text{—}\underset{\parallel}{\overset{O}{C}}\text{—}CH_2\text{—}O\diagdown\underset{\underset{CH_2OR_6}{CHOR_5}}{}X\diagdown O \text{ with HO above}$$

where

B is H or an N-terminal blocking group;

each $P_n$ is an amino acid residue, or is a heterocyclic replacement of the amino acid wherein the heterocycle is a piperazine, a decahydroisoquinoline, a pyrrolinone, a pyridine, a pyridone, a carbolinone, a quinazoline, a pyrimidone or the like;

m is 0 or a positive integer;

$R_5$ and $R_6$ are independently hydrogen, alkyl or acyl; and

X is N, S, O or $CH_2$.

In another embodiment, the cysteine protease inhibitor is of the formula:

$$B\text{—}(P_n)_{\overline{m}}\text{—}NH\text{—}\underset{R_1}{CH}\text{—}\underset{\parallel}{\overset{O}{C}}\text{—}CH_2\text{—}O\diagdown\underset{R_3}{\underset{R_2}{\diagdown}} O$$

where

B is H or an N-terminal blocking group;

each $P_n$ is an amino acid residue, or is a heterocyclic replacement of the amino acid wherein the heterocycle is a piperazine, a decahydroisoquinoline, a pyrrolinone, a pyridine, a pyridone, a carbolinone, a quinazoline, a pyrimidone or the like;

m is 0 or a positive integer;

$R_2$ and $R_3$ are indepentantly H or an alkyl or alkenyl group; and

X is N, S, O or $CH_2$.

In another embodiment, the cysteine protease inhibitors are of the formula:

$$B\text{—}(P_n)_{\overline{m}}\text{—}NH\text{—}\underset{R_1}{CH}\text{—}\underset{\parallel}{\overset{O}{C}}\text{—}CH_2\text{—}O\cdots\underset{R_7\ R_8}{\underset{R_6}{\underset{R_5}{}}} \underset{X}{\overset{R_4}{}} O$$

where

B is H or an N-terminal blocking group;

each $P_n$ is an amino acid residue, or is a heterocyclic replacement of the amino acid wherein the heterocycle is a piperazine, a decahydroisoquinoline, a pyrrolinone, a pyridine, a pyridone, a carbolinone, a quinazoline, a pyrimidone or the like;

m is 0 or a positive integer;

$R_4$ is a hydroxyl, alkoxyl, acyl, hydrogen, alkyl or phenyl;

$R_5$, $R_6$, $R_7$ and $R_8$ are independently hydrogen, alkyl, acyl, phenyl, halo, hydroxyl, oxy or alkoxy; and X is N, S, O or $CH_2$.

In another embodiment, the cysteine protease inhibitors are of the formula:

$$B\text{—}(P_n)_{\overline{m}}\text{—}NH\text{—}\underset{R_1}{CH}\text{—}\underset{\parallel}{\overset{O}{C}}\text{—}CH_2\text{—}O\cdots\underset{R_7\ R_8}{\underset{R_6}{\underset{R_5}{}}} \underset{X}{\overset{R_4}{}} O$$

where

B is H or an N-terminal blocking group;

each $P_n$ is an amino acid residue, or is a heterocyclic replacement of the amino acid wherein the heterocycle is a piperazine, a decahydroisoquinoline, a pyrrolinone, a pyridine, a pyridone, a carbolinone, a quinazoline, a pyrimidone or the like;

m is 0 or a positive integer;

$R_4$ is a hydroxyl, alkoxyl, acyl, hydrogen, alkyl or phenyl;

$R_5$ and $R_6$ may be attached to $R_7$ and $R_8$ to form a ring that is either saturated or unsaturated or aromatic; and X is N, S, O or $CH_2$.

In another embodiment, the cysteine protease inhibitors are of the formula:

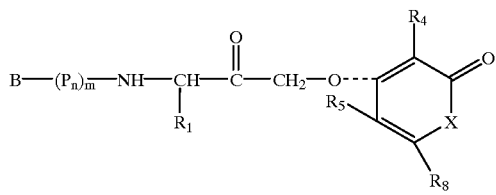

where

B is H or an N-terminal blocking group;

each $P_n$ is an amino acid residue, or is a heterocyclic replacement of the amino acid wherein the heterocycle is a piperazine, a decahydroisoquinoline, a pyrrolinone, a pyridine, a pyridone, a carbolinone, a quinazoline, a pyrimidone or the like;

m is 0 or a positive integer;

$R_4$ is a hydroxyl, alkoxyl, acyl, hydrogen, alkyl or phenyl;

$R_5$ and $R_8$ are independently hydrogen, alkyl, acyl, phenyl, halo, hydroxyl, oxy or alkoxy, or $R_5$ is attached to $R_8$ to form a homocyclic or hererocyclic ring that is either saturated or unsaturated or aromatic; and X is N, S, O or $CH_2$.

One object of the present invention is to provide improved cysteine protease inhibitors with improved solubility and toxicity profiles.

A further object of the present invention is to provide a class of cysteine protease inhibitors which are particularly effective for in vivo applications.

Further objects and advantages of the present invention will be apparent from the following description.

DESCRIPTION OF THE PREFERRED EMBODIMENT

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

As indicated above, the present invention relates to cysteine protease inhibitors which contain 1,3-dicarbonyl enolether leaving groups. In one aspect of the invention, a group of cysteine protease inhibitors which have been shown to be particularly effective for in vivo applications is disclosed.

The cysteine protease inhibitors described herein function as the sum of two portions. The first portion defines the specificity of a particular inhibitor to an enzyme by the spacial, hydrophobic or hydrophilic and ionic interactions of a particular composition that either imitates or improves upon the nature of the enzyme's natural substrate. The second portion is a trap that covalently binds the enzyme in a two-step mechanism: the first step involves the nucleophilic attack of the enzyme thiolate on the carbonyl of the inhibitor to form a hemithioketal. It is then energetically favorable for this intermediate to undergo a 1,2 migration of the thiolate in which an enolate (or enol form) of a 1,3-dicarbonyl is released. The enzyme has now become irreversibly bonded to the inhibitor. With the inhibitors of the present invention the leaving group is the enol form of a 1,3-dicarbonyl.

Accordingly, the cysteine proteinase inhibitors of the present invention are preferably constructed with an activated carbonyl which bears a suitable α-leaving group which is fused to a programmed peptide sequence that specifically directs the inhibitor to the active site of the targeted enzyme. (For example, Z-Phe-PheCHN$_2$ preferentially inhibits cathepsin L over cathepsin B.) Once inside the active site, this inhibitor carbonyl is attacked by a cysteine thiolate anion to give the resulting hemiacetal form. If the α-leaving group then breaks off, the bond between enzyme and inhibitor becomes permanent and the enzyme is irreversibly inactivated. The selectivity of the inhibitor for a particular enzyme depends not only on the "lock and key" fit of the peptide portion, but also on the reactivity of the bond binding the leaving group to the rest of the inhibitor. It is very important that the leaving group must be reactive to the intramolecular displacement via a 1,2-migration of sulfur in the breakdown of the hemithioacetal intermediate. The mechanism of protease inhibition is shown below in FIG. 1.

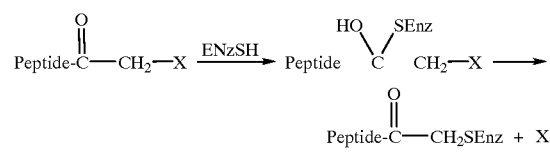

The preferred inhibitors of the present invention can be described generally by the formula:

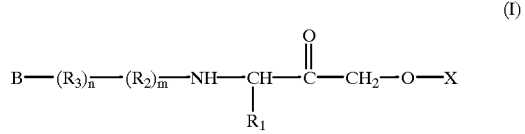

(I)

where

B is H or an N-terminal blocking group;

$R_{1-3}$ are the amino acid side chains of the $P_{1-3}$ amino acids, respectively;

n is 0 or 1;

m is 0 or 1; and

X is a five- or six-membered ring portion of the β-dicarbonyl enol ether leaving group, as further defined below.

In one embodiment, the compositions of the present invention are cathepsin or calpain inhibitors of the formula:

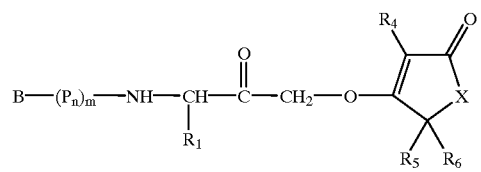

where

B is H or an N-terminal blocking group;

$R_1$ is the amino acid side chain of the $P_1$ amino acid residue; wherein the $P_1$ amino acid is not Asp;

each $P_n$ is an amino acid residue, or is a heterocyclic replacement of the amino acid wherein the heterocycle is a piperazine, a decahydroisoquinoline, a pyrrolinone, a pyridine, a carbolinone, a quinazoline, a pyrimidone or the like;

m is 0 or a positive integer;

$R_4$ is a hydroxyl, alkoxyl, acyl, hydrogen, alkyl or phenyl;

$R_5$ and $R_6$ are jointly a carboxyl group or a double bond terminating in an alkyl or an aryl group, or are independently acyl, aryl or heteroaryl if $R_4$ is hydrogen, alkyl or phenyl, or are independently acyl, alkyl, hydrogen, aryl or heteroaryl otherwise; and X is N, S, O or $CH_2$.

In another embodiment, the compositions of the present invention are ICE inhibitors of the formula:

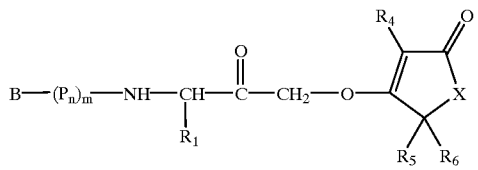

where
B is H or an N-terminal blocking group;
$R_1$ is the Asp amino acid side chain;
each $P_n$ is an amino acid residue, or is a heterocyclic replacement of the amino acid wherein the heterocycle is a piperazine, a decahydroisoquinoline, a pyrrolinone, a pyridine, a carbolinone, a quinazoline, a pyrimidone or the like;
m is 0 or a positive integer;
$R_4$ is a hydroxyl, alkoxyl, acyl, hydrogen, alkyl or phenyl;
$R_5$ and $R_6$ are jointly a carboxyl group or a double bond terminating in an alkyl or an aryl group, or are independently acyl, aryl or heteroaryl if $R_4$ is hydrogen, alkyl or phenyl, or are independently acyl, alkyl, hydrogen, aryl or heteroaryl otherwise; and
X is N, S, O or $CH_2$.

In another embodiment, the cysteine protease inhibitor is of the formula:

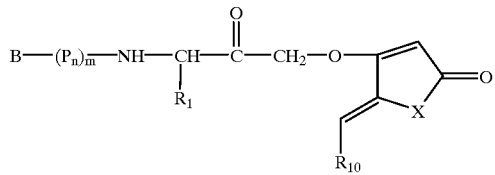

where
B is H or an N-terminal blocking group;
each $P_n$ is an amino acid residue, or is a heterocyclic replacement of the amino acid wherein the heterocycle is a piperazine, a decahydroisoquinoline, a pyrrolinone, a pyridine, a carbolinone, a quinazoline, a pyrimidone or the like;
m is 0 or a positive integer;
$R_4$ is a hydroxyl, alkoxyl, acyl, hydrogen, alkyl or phenyl;
$R_{10}$ is H or an optionally substituted alkyl, aryl, heteroaryl, or the residue of a sugar; and
X is N, S, O or $CH_2$.

In another embodiment, the cysteine protease inhibitor is of the formula:

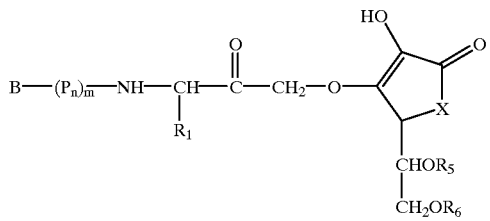

where
B is H or an N-terminal blocking group;
each $P_n$ is an amino acid residue, or is a heterocyclic replacement of the amino acid wherein the heterocycle is a piperazine, a decahydroisoquinoline, a pyrrolinone, a pyridine, a carbolinone, a quinazoline, a pyrimidone or the like;
m is 0 or a positive integer;
$R_5$ and $R_6$ are independently hydrogen, alkyl or acyl; and
X is N, S, O or $CH_2$.

Most preferably, $R_5$ and $R_6$ are each hydrogen. In one alternative embodiment the H on the hydroxyl group of the heterocyclic leaving group may be replaced by an alkyl or ankenyl group.

In another embodiment, the cysteine protease inhibitor is of the formula:

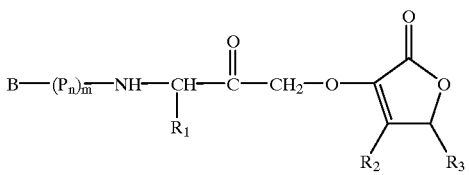

where
B is H or an N-terminal blocking group;
each $P_n$ is an amino acid residue, or is a heterocyclic replacement of the amino acid wherein the heterocycle is a piperazine, a decahydroisoquinoline, a pyrrolinone, a pyridine, a carbolinone, a quinazoline, a pyrimidone or the like;
m is 0 or a positive integer;
$R_2$ and $R_3$ are indepentantly H or an alkyl or alkenyl group; and
X is N, S, O or $CH_2$.

Most preferably $R_5$ is $CH_3$ and $R_6$ is $C_2H_5$ as shown in compound A2, infra.

In another embodiment, the cysteine protease inhibitors are of the formula:

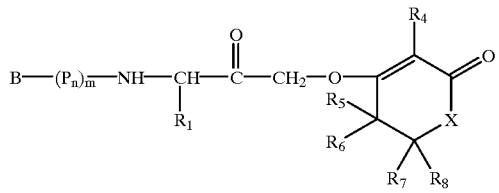

where
B is H or an N-terminal blocking group;
each $P_n$ is an amino acid residue, or is a heterocyclic replacement of the amino acid wherein the heterocycle is a piperazine, a decahydroisoquinoline, a pyrrolinone, a pyridine, a carbolinone, a quinazoline, a pyrimidone or the like;

m is 0 or a positive integer;

$R_4$ is a hydroxyl, alkoxyl, acyl, hydrogen, alkyl or phenyl;

$R_5$, $R_6$, $R_7$ and $R_8$ are independently hydrogen, alkyl, acyl, phenyl, halo, hydroxyl, oxy or alkoxy; and X is N, S, O or $CH_2$.

In another embodiment, the cysteine protease inhibitors are of the formula:

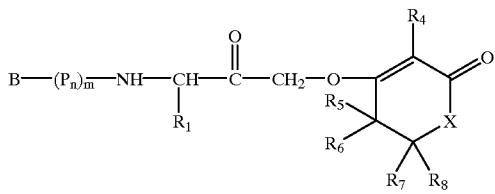

where

B is H or an N-terminal blocking group;

each $P_n$ is an amino acid residue, or is a heterocyclic replacement of the amino acid wherein the heterocycle is a piperazine, a decahydroisoquinoline, a pyrrolinone, a pyridine, a carbolinone, a quinazoline, a pyrimidone or the like;

m is 0 or a positive integer;

$R_4$ is a hydroxyl, alkoxyl, acyl, hydrogen, alkyl or phenyl;

$R_5$ and $R_6$ may be attached to $R_7$ and $R_8$ to form a ring that is either saturated or unsaturated or aromatic; and X is N, S, O or $CH_2$.

In another embodiment, the cysteine protease inhibitors are of the formula:

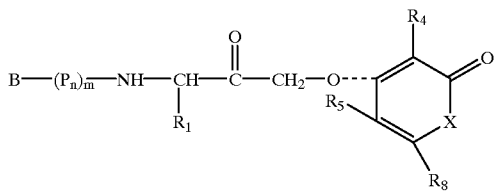

where

B is H or an N-terminal blocking group;

each $P_n$ is an amino acid residue, or is a heterocyclic replacement of the amino acid wherein the heterocycle is a piperazine, a decahydroisoquinoline, a pyrrolinone, a pyridine, a carbolinone, a quinazoline, a pyrimidone or the like;

m is 0 or a positive integer;

$R_4$ is a hydroxyl, alkoxyl, acyl, hydrogen, alkyl or phenyl;

$R_5$ and $R_8$ are independently hydrogen, alkyl, acyl, phenyl, halo, hydroxyl, oxy or alkoxy, or $R_5$ is attached to $R_8$ to form a homocyclic or heterocyclic ring that is either saturated or unsaturated or aromatic; and X is N, S, O or $CH_2$.

As to the amino acid blocking group B for the N-terminal amino acid nitrogen, many suitable peptide end-blocking groups are known in the art. For example the end-blocking groups identified in E. Gross and J. Meienhofer (eds.), *The Peptides,* Vol. 3 are generally suitable for use in the present invention. Preferred blocking groups include N-morpholine carbonyl and derivatives of propionic acid derivatives that have intrinsic analgesic or anti-inflammatory action. Examples of blocking groups having intrinsic analgesic or anti-inflammatory action may be found in Gilman, Goodman, Gilman, *The Pharmacological Basis of Therapeutics,* Sixth Ed. MacMillan, Chapter 29. As defined herein, the peptide end-blocking group is attached to either an amino acid or a peptide chain.

One particularly effective blocking group is the 4-morpholinylcarbonyl ("Mu") blocking group shown below:

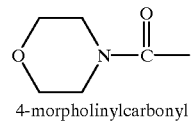

4-morpholinylcarbonyl

Other useful blocking groups include the morphine sulfonyl group and related groups as reported by Doherty et al. in "Design and Synthesis of Potent, Selective and Orally Active Fluorine-Containing Renin Inhibitors," 35 J. Med. Chem. 2. An appropriate blocking group for a particular inhibitor may be selected by persons skilled in the art without undue experimentation.

As is conventional in the art, and as used herein, amino acid residues are generally designated as $P_1$, $P_2$, etc., wherein $P_1$ refers to the amino acid residue nearest the leaving group, $P_2$ refers to the amino acid residue next to $P_1$ and nearer the blocking group, etc. In dipeptide inhibitors therefore, $P_2$ is the amino acid residue nearest the blocking group. In this disclosure the chain of amino acid residues is frequently written $(P_n)_m$ with each $P_n$ being an amino acid residue and m being zero or a positive integer. Each $P_n$ may, of course, be a different amino acid residue. Preferably, m is less than or equal to four. Most preferably, m is two.

As suggested above, any of the amino acid residues may be replaced by a heterocyclic replacement. Preferably the heterocycle is a piperazine, a decahydroisoquinoline, a pyrrolinone, a pyridine, a carbolinone, a quinazoline, a pyrimidone or the like. Persons skilled in the art may select an appropriate heterocycle in a manner similar to that in which appropriate amino acid residues are selected. As used herein therefore, terminology such as "the peptide portion" refers as well to the corresponding portion when heterocycles replace any or all of the amino acids.

The peptide portion of the inhibitor includes any peptide appropriate for targetting a desired cysteine protease. In particular, the side chain on the $P_1$ amino acid is selected according to the enzyme being targetted. For cathepsin B or L, this might include side chains such that the linked $P_1$ amino acid is a member of the group consisting of alanyl (Ala), arginyl (Arg), glutamic acid (Glu), histidyl (His), homophenylalanyl (HPhe), phenylalanyl (Phe), ornithyl (Orn), seryl (Ser) and threonyl (Thr), and optionally substituted analogues thereof such as thiazoles and amino thiazoles. Preferably the side chain on the $P_2$ amino acid is selected so that the linked $P_2$ amino acid is a member of the group consisting of phenylalanyl (Phe), leucyl (Leu), tyrosyl (Tyr) and valyl (Val) amino acid residues and substituted analogues thereof, particularly including Tyr(OMe).

More specifically regarding the selection of side chains, the cathepsins and the calpains share great cross reactivities with many inhibitors of structures shown above, although Cathepsin B responds most strongly to basic side chains at $P_1$ (although reacting to several), while Cathepsin L is more susceptible to neutral side chains at $P_1$. Both Cathepsin B and Cathepsin L require neutral side chains at $P_2$. Cathepsins H and C prefer to attach to unblocked peptides, with Cathepsin H favoring a single peptide, Cathepsin C a dipeptide and the calpains susceptible to neutral side chains. The cathepsins, as a general rule, are more reactive than the calpains. Interestingly, neither of these two enzyme types is inhibited when Asp occupies the $P_1$ position. In contrast, the interleukin-1β-converting enzyme (ICE) is unaffected by all these inhibitors unless Asp is at the $P_1$ position. This fundamental difference between the ICE enzyme and its inhibitors on the one hand, and the other cysteine enzymes and their inhibitors on the other, is well documented in the literature.

When an aspartyl side chain is present in inhibitors based on an activated ketone an unnatural event occurs—the free acid in the side chain attacks the ketone (whose counterpart in the natural substrate is an unreactive amide carbonyl) and a thermodynamically favored hemiketal results. Such hemiketals may be transition state mimics that are also known to play a role in protease inactivation. The inhibition of the ICE enzyme can now follow either of two paths: hemiacetal exchange or thiolate attack on unmasked ketone, thus leading to some confusion in the detailing of the mechanism of inhibition. The problem is eliminated by esterification of the side chain.

One optimum peptide sequence for ICE inhibitors is known to be: B—Tyr—Val—Ala—Asp—Trap (SEQ ID NO:1); where B is the blocking group and the "trap" is the activated ketone or aldehyde (reversible inhibitor). Dolle has shown that this sequence can be reduced to Val—Ala—Asp—and even Asp alone is inhibitatory. Dolle et al., $P_1$ Aspartate—Based Peptide α-((2,6-Dichlorobenzoxy)oxy) methyl Ketones as Potent Time-Dependent Inhibitors of Interleukin-1β-Converting Enzyme, 37 *J. Med. Chem.* 563.

The leaving groups of the present invention share certain features to assure the low toxicity and good solubility of the inhibitors. In particular, the leaving groups of the present invention: (1) immitate or improve upon the cleaved peptide portion of the proteases natural substrate; (2) activate the carbonyl of the inhibitor to selectively react with the thiolate of a cysteine protease; (3) are non-toxic and non-cleavable by non-cysteine proteases and esterases; and (4) are very water soluble and enable the use of more amino acids than prior art leaving groups allow.

As indicated, the inhibitors of the present invention immitate or improve upon the cleaved peptide portion of the proteases natural substrate. The natural substrate leaving group is the sum of planar (or nearly so) amide bonds fused by tertiary substituted chiral carbon atoms. In applicant's prior application (Ser. No. 08/164,031) it was disclosed that oxygen fused to a heterocyclic ring could imitate the planar features of the natural substrate leaving groups, and also that a heterocycle unit provides the diversity needed to imitate the different electronic and spacial specificity requirements of different individual enzymes. It was also demonstrated that the degree of aromaticity of the ring was not a requirement for efficacy.

The inhibitors of the present invention activate the carbonyl of the inhibitor to selectively react with the thiolate of a cysteine protease. This concept was not appreciated until the demonstration of the success of peptidyl fluoroketones by Rasnick et al. in U.S. Pat. No. 4,518,528. The best replication of the chemistry ascribed to the most electronegative atom is to replace fluorine with the second most electronegative atom (oxygen) deshielded further by the attachment of an atom with electron withdrawing double bond character. The inhibitors of this invention maximize this premise by electronically coupling the anion of the leaving group to the electo positive center of a carbonyl carbon. By using a hydrocarbon structure devoid of halogens we eliminate the toxicity associated with peptidyl fluoroketones, trifluoromethyl substitutions, and halogenated hydrocarbons which are common to other inhibitors in the art.

The inhibitors of the present invention are non-toxic and non-cleavable by non-cysteine proteases and esterases. In an attempt to minimize dipole moments, 1,3-dicarbonyls form very stable enols, and as a result the α-ketoethers prepared in this invention show outstanding stability and oral efficacy. On the other hand, 1,3-dicarbonyls are readily eliminated through the Krebs Cycle and therefore pose less of a toxicity potential than nitrogen aromatic heterocycles and other aromatics that require liver oxidative clearance.

The inhibitors of the present invention are preferably very water soluble and enable the use of more amino acids than current art leaving groups in the peptide construction of the inhibitor. One generalization that can be made about the state of the art inhibitors is that the leaving group is of high molecular weight (as a dichlorophenol) which reduces the overall water solubility and oral efficacy of the peptide inhibitor. The smaller more polar oxyheterocycles of this invention actually increase the water solubility of the peptide inhibitor as shown in Example 8 where the leaving group derived from tetronic acid increases the solubility of the peptide inhibitor almost two fold over that of the peptide portion alone (approximated by the fluoroderivative). Further additions of hydroxyl groups to the parent tetronic nucleus further enhances water solubility and leaving groups such as those derived from ascorbic acid becomes most preferable.

Reference will now be made to specific examples for making and using the cysteine protease inhibitors of the present invention. It is to be understood that the examples are provided to more completely describe preferred embodiments, and that no limitation to the scope of the invention is intended thereby.

EXAMPLE 1

N-Morpholinecarbonyl-L-phenylalanyl-L-homophenylalanine-α-(4-oxy-5-phenyl-4-cyclopentene-1,3-dione) methyl ketone N-morpholinecarbonyl-L-phenylalanyl-L-homophenylalanine bromomethyl ketone (100 mg, 0.194 mmol), potassium fluoride (45 mg, 0.775 mmol), and 4-hydroxy-5-phenyl-4-cyclopentene-1,3-dione was placed in a 20 cm test tube equipped with a stirring bar and placed under an argon atmosphere. Next 3 ml of dry DMF was syringed into the reaction which was allowed to stir at room temperature until TLC (silica gel, $CHCl_3$/isopropanol:95/5) showed total loss of starting material. The reaction was then passed through a short plug of silica gel (ethyl acetate) and the solvent was removed in vacuo. The resulting material was purified by size exclusion chromatography (LH 20, methanol) and precipitated in ether to give a yellow powder after filtration. (m.p.=155–157° C., $IC_{50}$ Cathepsin B, 94 nM.)

EXAMPLE 2

N-Morpholinecarbonyl-L-phenylalanyl-L-homophenylalanyl-α-(4-ascorbityl) methyl ketone N-morpholinecarbonyl-L-phenylalanine bromomethylketone (495 mg, 1 mmol), sodium ascorbate (380 mg, 2 equivalents), and potassium fluoride (116 mg, 2 equivalents) was placed in a 50 mL round bottom flask under an atmosphere of argon. Next, 5 ml of dry DMF was syringed in and the reaction was allowed to stir at room temperature overnight The next day the reaction was filtered through celite and the solvents were removed in vacuo. The residue was dissolved in chloroform and the resulting solution was diluted with an equal volume of methylene chloride to precipitate the unreacted sodium ascorbate. After filtration the solvent was removed in vacuo and the residue purified by size exclusion chromatography to give a white solid, mp 105–110° C. $IC_{50}$ Cathepsin B, 141 nM.

In a similar manner the following compounds were prepared: N-Morpholinecarbonyl-L-phenylalanyl-L-homophenylalanyl-α-(4-oxy-6-methyl-2-pyrone) methyl ketone (m.p. 94–98° C.); N-Morpholinecarbonyl-L-phenylalanyl-L-homophenylalanyl-α-(4-oxy-5,6-dihydro-6-methyl-2H-pyran-2-one) methyl ketone (m.p. 74–78° C.); N-Morpholinecarbonyl-L-Leucyl-L-homophenylalanyl-α-(4-oxy-(6-methyl-2-pyrone) methyl ketone (m.p. 70–75° C.); N-Morpholinecarbonyl-L-phenylalanyl-L-homophenylalanyl-α-(4-oxy-coumarin) methyl ketone (m.p. 115–119° C.); N-Morpholinecarbonyl-L-phenylalanyl-L-lysyl-(4-oxy-(6-methyl-2-pyrone) methyl ketone (m.p. 151–155° C.); N-Morpholinecarbonyl-L-tryosyl (O-methyl)-L-lysyl-(4-oxy-(6-methyl-2-pyrone) methyl ketone (m.p. 140–142° C.); N-Morpholinecarbonyl-L-phenylalanyl-L-homophenylalanyl-α-(4-oxy-3-phenyl-dihydrofuran-2-one) methyl ketone (m.p. 114–116° C.); N-Morpholinecarbonyl-L-tryosyl (O-methyl)-L-lysyl-(4-oxy-3-phenyl-dihydrofuran-2-one) methyl ketone (m.p. 140–142° C.); N-Morpholinecarbonyl-L-phenylalanyl-L-lysyl-α-(4-oxy-3-phenyl-dihydrofuran-2-one) methyl ketone (m.p. 140–145° C.); N-Morpholinecarbonyl-L-phenylalanyl-L-homophenylalanyl-α-(4-oxy-dihydrofuran-2-one) methyl ketone (m.p. 155–157° C.).

Structural formulas and in vitro activities (against Cathepsin B) for these compounds are set forth below:

| In Vitro Activity Against Purified Cathepsin B | |
|---|---|
| Compound | $IC_{50}$ Cat B |
| 1. Mu Phe Hphe CH₂O— [structure] | 94 nM |
| 2. Mu Phe Hphe CH₂O— [structure with OH, CHOH, CH₂OH] | 141 nM |
| 3. Mu Phe Hphe CH₂O— [structure with CH₃] | 112 nM |
| 4. Mu Phe Hphe CH₂O— [structure with CH₃] | 567 nM |
| 5. Mu Leu Hphe CH₂O— [structure with CH₃] | 400 nM |
| 6. Mu Phe Hphe CH₂O— [coumarin structure] | 45 nM |
| 7. Mu Phe Lys CH₂O— [structure with CH₃] | 25 nM |
| 8. Mu Tyr(OMe)Lys CH₂O— [structure with CH₃] | 83 nM |
| 9. Mu Phe Hphe CH₂O— [structure] | 36 nM |

-continued

In Vitro Activity Against Purified Cathepsin B

| | Compound | IC$_{50}$ Cat B |
|---|---|---|
| 10. | Mu Tyr(OMe) Lys CH$_2$O— 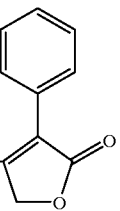 | 8 nM |
| 11. | Mu Phe Lys CH$_2$O— 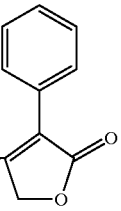 | 5 nM |
| 12. | Mu Phe Hphe CH$_2$O— 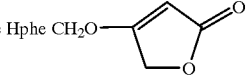 | 10 nM |

EXAMPLE 3

Protocol for the In Vitro Evaluation of Inhibitors with Cathepsin B

Enzyme: Cathepsin B, purified from human liver, is from Enzyme Systems Products (Dublin, Calif.). The activity is 50 mU per ml at 30° C., in 52 mM sodium phosphate, pH 6.2, 31 mM DTT, 2.1 mM EDTA, with 0.2 mM Z-Arg-Arg-7-amino-4-trifluoromethyl-coumarin as a substrate. Specific activity is 8330 mU per mg protein. (1 mU=1 nmol per min.)

Substrate Boc-Leu-Arg-Arg-7-amino-4-trifluoromethyl-coumarin-2HBr is from Enzyme Systems Products (Dublin, Calif.) and is known to be a specific substrate for cathepsin B. A 20 mM solution is made in DMF and stored at 20° C.

Candidate inhibitors are dissolved in DMF and diluted to 20 mM and stored at 20° C. Dilutions are made in assay buffer.

The percent inhibition and the inhibitor concentration at which the enzyme is 50% inhibited (IC$_{50}$) are determined as follows. Five μl of assay buffer (50 mM potassium phosphate pH 6.2, 2 mM EDTA, 5 mM DTT) on ice for 30 min. The inhibition is initiated by the addition of 5 ml of 200 mM, 20 mM, and 2 mM inhibitor each to the 480 μl aliquots. The 485 μl aliquot with enzyme is used as a control and thus receives no inhibitor. The enzyme/inhibitor mixtures are incubated 10 min. on ice and assayed for cathepsin B activity as follows: Cathepsin B assay: To 490 μl of pre-incubated inhibitor/enzyme mixtures in assay buffer in 0.5 ml cuvette at 37° is added 10 μl of the substrate. Final inhibitor concentrations become 2000 nM, 200 nM, and 20 nM for the 200 μM, 20 μM and 2 μM stock concentrations, respectively. Activity is followed by release of free AFC over 5 min. The change in fluorescence is (fluorescence units at t=6)−(fluorescence units at t=1) with a Perkin-Elmer LS-5B spectrofluorometer (ex=400 nm, em=505 nm). The percent inhibition is determined by comparing the change in fluorescence units of the three sample concentrations of inhibited enzyme to the change in fluorescence units of the control enzyme. The percent inhibition is calculated as:

100−(fl. units of sample/fl. units of control×100).

The IC$_{50}$ is ascertained by plotting percent inhibition vs. inhibitor concentration on the log scale. The IC$_{50}$ is the concentration of the inhibitor (nM) at which the enzyme is inhibited by 50%.

IC$_{50}$ values for preferred inhibitors are shown on the table of structural formulas supra.

EXAMPLE 4

TABLE 1

| Malarial Cysteine Protease Inhibition: IC$_{50}$ Concentrations[1] | | |
|---|---|---|
| New Inhibitor | P. falciparum | P. vinckei |
| 6. | 5–10 nM | 5–10 nM |
| 7. | ~50 nM | ~100 nM |
| 9. | 300–500 pM | <1 nM |
| 11. | 5–10 nM | ~10 nM |
| 12. | ~10 nM | ~10 nM |

[1]The IC$_{50}$ is the concentration of the inhibitor (nM) at which the enzyme is inhibited 50% within 6 minutes in our standard in vitro assay (see Example 3).

Proteolytic activity assays. Gelatin-substrate PAGE is performed described in Rosenthal, McKerrow, Rasnick, and Leech, Plasmodium falciparum: Inhibitors of Lysosomal Cysteine Proteinases Inhibit a Trophozoite Proteinase and Block Parasite Development, 35 Mol. Biochem. Parasitol. 177–184 (1989). In brief, this technique involves electrophoresis of nonreducd proteins on a gelatin-containing gel, removal of SDS from the gel by washing with 2.5% Triton-100, overnight incubation (0.1 M sodium acetate, 10 mM dithioerythritol (pH 6.0, 37° C.) of the gel to allow hydrosis of the gelatin by renatured proteinases, and staining with Coomassie blue. Proteinases are identified as clear bands in the blue staining gel. To evaluate the effects of proteinase inhibitors, the inhibitors are incubated with parasite extracts (1 hr, room temperature) before samples are mixed with the electrophoresis sample buffer, and they are included in the overnight gel incubation buffer. Proteolytic activity was also measure with two other substrates: (a) fluorogenic peptides-ubstrates containing the 7-amino-4-methyl-coumarin (AMC) detecting group (Enzyme Systems Products, Dublic, Calif.) and (b) [$^{14}$C]-methemoglobin (Dupont New England Nuclear, Wilmington, Del.), both as described in Rosenthal, McKerrow, Aikawa, Nagasawa, and Leech, A Malarial Cysteine Proteinase is Necessary for Hemoglobin Degradation by Plasmodium Falciparum. 82 J. Clin. Invest. 1560–66. (1988).

In another test of malarial inhibition by the cysteine protease inhibitors of the present invention compound A2, infra, was particularly effective.

EXAMPLE 5

TABLE 3

Inhibition of *T. cruzi* in Infected Cells with New Inhibitors.

| | Survival Time | |
|---|---|---|
| Compound | Cell line J774 | Cell line BHK |
| Control | 4 Days | 5 Days |
| Mu Phe HPheCH$_2$F | 16 Days plus | 16 Days plus |
| 6. | 16 Days plus | 16 Days plus |
| 9. | 4 Days | 6 Days |

Survival time is measured in days before the cell monolayer is destroyed by the infection. Irradiated BHK and J774 cells (six well plates) were infected with *T. cruzi* and simultaneously treated with 20 μM (3 ml total volume) with daily change of culture medium+plus inhibitor).

Cultivation and preparation of *T. cruzi*. Cloned and uncloned populations were derived from the strains Brasil and CA-I and are cryopreserved in liquid nitrogen. Axenically cultured epimastigotes are maintained in exponential growth phase by weekly passage in Brain Heart Infusion-Tryptose medium (BHT media as given in Cazzulo, Cazzulo, Martinez, and Cazzulo, Some Kinetic Properties of a Cysteine Proteinase (Cruzipain) from Trypanosoma Cruzi. 33 *Mol. Biochem. Parasitol.* 33–42 (1990)), supplemented with 20 μg/ml and 10% (v/v) heat inactivated fetal calf serum (FCS). Different host cell lines (J774 mouse macrophage, BHK, etc.) are cultured with RPMI-1640 supplemented with 5% FCS at 37° in a humidified atmosphere containing 5% CO$_2$. Trypomastigotes liberated from the host cells are used to infect new cultures for serial maintenance of the parasite in cell culture. The protocols used for the in vitro assays of cysteine protease inhibitors are essentially as described by Harth, Andrews, Mills, Engel, Smith, and McKerrow, Peptide-Fluoromethyl Ketones Arrest Intracellular Replication and Intercellular Transmission of Trypanosoma Cruzi. 58 *Mol. Biochem. Parasitol.* 17–24 (1993), with the exception that in some experiments, the host cells are irradiated (2400 RADs) before infection to prevent them from dividing.

EXAMPLE 6

In Vitro Inhibition of *Pneumocystis carinii*

When the following compounds were tested in a *Pneumocystis carinii* culture system with human embryonic lung fibroblast monolayers, the organism proliferation was inhibited as demonstrated below. The percent of inhibition is calculated as 100-(the number of *P. carinii* trophozoites in a treated cell culture/number of trophosites of the control)× 100.

| | Percent Inhibition | | | |
|---|---|---|---|---|
| Compound | Day 1 | Day 3 | Day 5 | Day 7 |
| Control | 0 | 0 | 0 | 0 |
| 3 | 23 | 44 | 39 | 13 |
| 9 | 17 | 67 | 64 | 65 |

Methods

The drugs dissolved in dimethyl sulfoxide were diluted to concentrations of 10 μg/ml for compound 3 and 10 μM/ml for compound 9 in minimum essential medium used for the culture of human embryonic lung fibroblasts. The final maximum dimethyl sulfoxide concentration was 0.1%, a concentration of dimethyl sulfoxide that did not affect *P. carinii* proliferation when it is used alone and that gave *P. carinii* growth curves comparable to those of organisms in untreated control wells. Cell cultures in 24-well plates were innoculated with *P. carinii* trophozoites (final concentration, about 7×10$^5$ per ml) obtained from infected rat lungs. Each culture plate contained untreated and treated wells. Plates were incubated at 35° C. in a gas mixture of 5% O$_2$, 10% CO$_2$, 85% N$_2$ for up to 7 days. Plates were sampled on days 1, 3, 5 and 7 by removal of 10 μl amounts after agitation of the cultures. The samples were placed on slides in 1-cm$^2$ areas, fixed in methanol and stained with Giemsa stain; and then they were examined microscopically as unknowns by two individuals. For each parameter there were four wells, making eight values for each parameter. Standard errors range from 3–13%. Cultures were spiked with fresh drugs on days 2, 4 and 6.

EXAMPLE 7

The in vivo inhibition of cathepsin B in rat liver

| | Time Post Dose (Hours) | | | | |
|---|---|---|---|---|---|
| Compound | 1.5 | 3 | 6 | 12 | 24 |
| | (via stomach tube). | | | | |
| 6 | 48 | 29 | N/A | 30 | 0 |
| 12 (1600 nM dose) | | 53 | 32 | | |
| 12 (800 nM dose) | | 35 | 31 | | |
| | (via injection, IP) | | | | |
| 12 (1600 nM dose) | | 79 | 70 | | |
| 12 (800 nM dose) | | 55 | 70 | | |

Protocol for the in vivo Evaluation of Inhibitors. Female Sprague Dawley rats (150–200 g each) are purchased from Simonson, Gilroy, Calif. After 1 week of acclimation in-house, the animals (usually four per group) are dosed by the selected route of administration. Test compounds are dissolved in ethanol and diluted to the appropriate concentration with water. In control studies, animals are dosed only with ethanol water vehicle.

Tissue Homogenate Preparation. At the appropriate time post dose, the treated animals are anesthetized with ether, decapitated and exsanguinated. The tissues of interest are removed, quickly frozen in liquid nitrogen and then are stored at −70° C. until processing. All subsequent manipulations of the tissue samples are carried out at 4° C. Liver and skeletal muscle are pulverized while still frozen and then homogenized, while other target tissues are homogenized without prior pulverization. The tissue homogenization, in distilled water or 0.1% Brig-35, are subsequently performed using three 15-s bursts with a 10 N probe on a Tekmar Tissuemizer set to 75–80% power. The samples are centrifuged at 15000 g for 40 min; they partition into a lipid layer, a lower clarified layer and a solid pellet. The clarified supernatant is carefully aspirated and transferred to clean polypropylene tubes for storage at −70° C., until the fluorometric assay for enzyme activity can be performed.

Purified Lysosomal Enzyme Preparation. The procedure is based on a report by Bohley et al. (1969) and Barrett and Kirshke (1981). At the appropriate time post dose, the treated animals are anesthetized with sodium barbital and the livers are perfused in situ with ice-cold saline. The livers are then removed, rinsed with ice-cold saline, blotted and weighed. The animals are sacrificed with ether. All subsequent manipulations of the tissue samples are carried out at 4° C. The livers are homogenized in 2 volumes of 0.25M sucrose at 0° C. with a 30 ml Wheaton Teflon-on-glass homogenizer, using five full strokes with a motor setting at 55. Following centrifugation at 600 g for 10 minutes, the supernatant is transferred to clean tubes for centrifugation at 3000 g for 10 minutes. The resulting supernatant is centrifuged for 15 minutes. The lysosomal pellet is washed twice with 0.25 M sucrose, lysed in 2.5 volumes of distilled water using a glass-on-glass homogenizer, and then centrifuged at 1000 g for 60 minutes. The supernatant is stored at −70° C. until fluorimetric assay for enzyme activity is performed.

EXAMPLE 8

Aqueous solubilities of Morpholinecarbonyl-phenylalanyl-homophenylalanyl-α-(4-oxy-dihydrofuran-2-one) methyl ketone vs. Morpholine-carbonyl-phenylalanyl-homophenylalanyl-fluoromethylketone The aqueous solubilities of the two title compounds at 20° C. were determined by using UV spectroscopy and compared to that of a known standard benzoxycarbonyl-phenylalanyl-alanylfluoromethyl ketone. The aqueous solubility of Mu-Phe-HPhe-α-(4-oxy-dihydrofuran-2-one) methyl ketone 12 was measured to be 0.277 mg/ml. The aqueous solubility of Mu-Phe-HPhe-$CH_2F$ was measured to be 0.140 mg/ml. The aqueous solubility of Z-Phe-Ala-$CH_2F$ was 0.045 mg/ml at 14° C.

Experimental

A saturated solution was prepared by weighing 10 mg of the material and placing it in 5 ml of distilled and deionized water. The solution was capped and stirred at 20° C. unless otherwise noted. A 1 ml aliquot was removed after 24 hours and was filtered through a 0.45 μm filter and diluted 1:50 with distilled and deionized water. Subsequent aliquots were taken and similarly diluted after 48, 72, and 96 hours respectively. The absorbances were measured at 247 nm for compound 12 and at 219 nm for Mu-Phe-HPhe-$CH_2F$ and were compared against a series of respective standard solutions run under similar conditions.

EXAMPLE 9

Synthesis of the Cathepsin H Inhibitors

L-Homophenylalanyl-α-(4-oxy-(6-methyl-2-pyrone) methyl ketone.

BOC-homophenyl-bromomethylketone (300 mg), potassium fluoride (195 mg), potassium carbonate (233 mg) and 4-hydroxy-6-methyl-2-pyrone (212 mg) was placed in a round bottom flask under an atmosphere of argon. About one mL of DMF was added and the mixture was stirred at 50° C. for 40 min. The reaction was then diluted with ethyl acetate (10×) and passed through a plug of silica gel to remove the salts. The solvents were removed under vacuum. The BOC-protecting group was removed by dissolving the resulting solid in 3 mL of methylene chloride and adding 3 mL of 4N HCl-dioxane. The reaction was run until only a stationary spot was detected with silica gel TLC (9:1, $CHCl_3$:isopropanol). The resulting mixture was then added dropwise to 50 mL of ether and the precipitated solid was filtered. mp. 177–179° C. $IC_{50}$ Cathepsin H: 118 nM.

In the same manner L-Homophenyl-α-(4-oxy-dihydrofuran-2-one)methyl ketone hydrochloride was synthesized. mp. 128–132° C. $IC_{50}$ Cathepsin H: 251 nM.

Numerous other cathepsin H inhibitors can be made with the construction of an unblocked amino acid on an α-oxy heterocycle methyl ketone.

EXAMPLE 10

Synthesis of Ice Inhibitors

The following example is meant to be illustrative but is not meant to be restrictive to other variations which would involve exchanges of blocking groups, abbreviation or minor alterations in side chain construction, or exchanges with other leaving groups of this invention.

N-Benzoxycarbonyl-valyl-alanyl-aspartyl-α-(4-oxy-(6-methyl-2-pyrone) methyl ketone Z-Val-AlaOMe:

N-Benzoxycarbonyl-valine was dissolved under argon in 300 mL of freshly distilled THF and the resulting solution was cooled in a mathanol-ice bath. One equivalent of N-methyl morpholine followed by one equivalent of isobutylchloroformate was added and the reaction was allowed to activate for 20 minutes. Another equivalent of N-methylmorpoline is then added followed by one equivalent of solid alanine methyl ester hydrochloride salt. The reaction was allowed to come slowly to room temperature and stir overnight. The next day the reaction was poured into 200 mL of 1N hydrochloric acid and extracted with ethyl acetate (2×150 mL). The combined organic fractions were washed with brine (50 mL), aqueous sodium bicarbonate (100 mL), dried over $MgSO_4$, filtered and the solvents were removed under reduced pressure to give 14 g of a white solid methyl ester. mp. 157–163° C.

Hydrolysis of the methyl ester was effected by dissolving 2.20 g in 35 mL of methanol followed by the addition of 8.2 mL of 1N aqueous sodium hydroxide solution. The reaction was stirred at room temperature for 4 hours. At this time TLC (silica gel/$CHCl_3$/isopropanol) showed that most of this material had been converted to the acid (stationary spot on TLC). The methanol was then removed under reduced pressure and the residue was dissolved in water (100 mL) an additional 5 mL of sodium hydroxide was added and the water was washed with ethyl acetate (50 ml) and then neutralized with 1N hydrochloric acid, and extracted with 2×100 ml of ethyl acetate. The organic layer was dried over $MgSO_4$, filtered and the solvents were evaporated to give a white solid: mp. 170–175° C.

Condensation with aspartyl (O-t-butyl)-O-methyl ester was effected as follows:

Z-Val-Ala-OH was dissolved in 300 mL of freshly distilled THF and the resulting solution was cooled in an ice-methanol bath. Next one equivalent of N-methyl morpholine was added followed by one equivalent of isobutylchloroformate and the reaction was allowed to activate for 20 minutes. Another equivalent of N-methyl morpoline was added followed by one equivalent (5 g) of HCl-Asp(OtBu)OMe. The mixture was allowed to come slowly to room temperature and stir overnight. The next day the reaction was poured into 200 ml of 1N hydrochloric acid and extracted with ethyl acetate. The organic layer was washed with sodium bicarbonate (aq, 50 mL), brine (50 mL) and the organic layer was dried over $MgSO_4$, filtered, and the solvents were removed under reduced pressure. The residue was crystallized from 50 mL of methylene chloride and 200 mL of ether to give white crystals (4.0 g), mp. 157–163° C.

Hydrolysis to Free Acid:

Z-Val-Ala-Asp(otBu)OMe (4.6 g) was dissolved in 30 mL methanol and then 12 mL of 1N sodium hydroxide (aq) was added and the reaction was stirred for 1 hour at room temperature. At the end of this time the methanol was removed under reduced pressure and 50 ml of water plus another 12 mL of 1N solium hydroxide was added to dissolve the precipitated solid. The resulting water solution was washed with ethyl acetate (50 mL) and then the water fraction was acidified with 1N HCl and the resulting mixture extracted with ethyl acetate, dried over $MgSO_4$, filtered and concentrated to give 3.74 g of Z-Val-Ala-Asp(O-tBu)OH.

Conversion to the Diazoketone:

Z-Val-Ala-Asp(O-tBu)OH was dissolved in 200 mL of freshly distilled THF and a methanol-ice bath was applied. Next one equivalent of N-methyl morpholine followed by one equivalent of isobutyl chloroformate was added and the reaction was allowed to activate for 20 minutes and then the resulting mixture was poured through filter paper into diazomethane/ether made from 6.3 g of Diazald (Aldrich) according to the supplier's directions. The reaction was allowed to stand overnight and then worked up in the following way: The reaction was washed with water (2×50 mL), sodium bicarbonate (50 mL), brine (50 mL) and then dried over $MgSO_4$, filtered and the solvents were removed under reduced pressure to give a yellow solid 3.75 g. This residue was then chromatographed in two parts through a 1×12 inch silica gel ($CHCL_3$:isopropanol/95:5) column to give two product fractions. The product with the lower $R_f$ value (0.3) was shown by the absorption at 5.54 ppm in the 100 MHz NMR to be the correct product.

Conversion to the Bromoketone:

Z-Val-Ala-Asp(OtBu)$CHN_2$ was dissolved in 25 mL ether and 25 mL THF and a methanol-ice bath was applied. Next 0.1 mL HBr/acetic acid (30%) diluted to 10 mL with ether:THF (1:1) was added dropwise. The yellow solution becomes clear and when no more color remains the reaction is poured into an equal volume of brine, the organic layers are separated and the water fraction is washed with an additional 50 mL THF:ether. The organic fraction was then washed with 50 mL of aqueous sodium bicarbonate, 50 mL brine, dried over $MgSO_4$, filtered and concentrated to give a white solid: mp. 150–151° C.

Conversion to the α-(4-oxy-(6-methyl-2-pyrone) methyl ketone:

Z-Val-Ala-Asp(otBu)$CH_2$Br (131 mg), 4-hydroxy-6-methyl-pyrone (58 mg, 2 equivalents), potassium fluoride (53 mg), and 1.5 mL of DMF was stirred at room temperature for two hours at which time TLC (silica gel, $CH_3Cl$/isopropanol:97/3) showed loss of starting material and development of product. The reaction was then run through a plug of silica gel ($CHCl_3$/isopropanol/9:1) and the solvents were removed under reduced pressure. Most of the excess pyrone starting material was precipitated from isopropyl ether: $CH_2Cl_2$ and the Z-Val-Ala-Asp(OtBu)-α-(4-oxy-6-methylpyrone) methyl ketone was isolated from the resulting mother liquor by removal of the solvent and size exclusion chromatography: NMR (100 MHz, $CDCl_3$) δ 0.9 (dd, 6), 1.4 (broad s+d, 12), 2.1 (s, 3), 3.5 (s, 2), 5.1 (s, 2), 7.3 (m, 5).

Removal of the side chain t-butyl group:

Z-Val-Ala-Asp(OtBu)$CH_2$O-(6-methyl-pyrone) was dissolved under argon in 2 ml of methylene chloride add 2 mL of 50% trifluoroacetic acid methylene chloride was added and the resulting clear solution was stirred for 30 minutes. At this time silica gel TLC ($CHCl_3$/isopropanol:9/1) showed loss of starting material (starting material $R_f$ 0.66; product $R_f$ 0.44). The reaction was diluted twofold with chloroform and the solvents and reagents removed under reduced pressure to give a white solid, mp. 158–163° C. (with multiple phase changes prior to melting).

Synthesis of N-Morpholinecarbonyl-L-valyl-L-Alanyl-Aspartyl (OtBu)-α-(ascorbityl) methylketone N-Morpholinecarbonyl-L-aline methyl ester:

HCL-Valine methyl ester (25 g) was dissolved under argon in 600 mL of freshly distilled THF and 100 mL of dry DMF and 1.0 equivalents of N-methyl morpholine. The resulting solution was cooled to −15° and an additional 1.1 equivalent of N-methyl morpholine followed by 1.1 equivalents of morpholine chloride was added. The reaction was allowed to come slowly to room temperature and stir overnight. The reaction is then poured into 300 mL of 1N HCL and extracted with ethyl acetate (2×200 mL). The combined organic fractions were washed with 1N HCL (50 mL), brine (50 mL), dried over $MgSO_4$, filtered and the solvents were removed under reduced pressure to give 33 g of N-morpholinecarbonyl-valine methyl ester as a white solid: NMR (100 MHz, $CDCl_3$ δ 0.9 (dd, 6), 2.1 (septet, 1), 3.0 and 3.65 (morpoline triplets, 4 and 4), 4.98 (N-H).

Conversion to Mu-Val-OH:

The above methyl ester was dissolved in 300 mL of methanol and 157 mL of 1N aqueous sodium hydroxide was added. The reaction was stirred at room temperature for 2 hrs. after which time TLC showed the product as a stationary spot. The methanol was removed under reduced pressure and an additional 28 mL of 1N aqueous sodium hydroxide was added and the water fraction was washed with ethyl acetate (75 mL). The water fraction was then acidified with 185 mL of 1N HCl, ¾ of the water was removed under reduced pressure and the resulting mixture was extracted with ethyl acetate (2×300 mL). The organic fraction was washed with 1N HCl (50 mL), brine (50 mL), dried over $MgSO_4$, filtered and concentrated to give N-morpholinecarbonyl-valine 29.75 g (78% yield).

Condensation with Alanine methyl ester:

Mu-Val-OH was dissolved in 300 mL of freshly distilled THF under argon and the solution was cooled to −15° C. Next one equivalent of N-methyl morpholine followed by one equivalent of isobutylchloroformate was added. The reaction was allowed to activate 20 minutes and then another equivalent of N-methyl morpholine followed by alanine methyl ester hydrochloride salt was added. The reaction was allowed to come slowly to room temperature and to stir overnight. The next day the reaction was poured into 1N hydrochloric acid and extracted with ethyl acetate (2×200 mL). The combined organic layers were washed with 1N hydrochloric acid (50 mL), brine, dried over $MgSO_4$, filtered, and the solvents were removed under reduced pressure to give 10.74 g (78%) of N-morpholinecarbonyl-valyl-alanyl methyl ester. NMR (100 MHz, $CDCl_3$) δ 1.4 (d, Ala $CH_3$), 3.7 (s, OMe) ppm.

Hydrolysis to the Free Acid:

Mu-Val-Ala-OMe (1 g) was dissolved in 15 mL of methanol and then 4.8 mL of 1N sodium hydroxide (aq) was added. The reaction was allowed to continue until TLC (CHCl₃/isopropanol:9/1) showed only a stationary spot. The methanol was then removed under reduced pressure and an additional 1.2 mL of ethyl acetate and the water fraction was acidified with 6 mL of 1N HCl. The mixture is extracted with about 50 mL of ethyl acetate and the organic fraction washed with 5 ml of 1N HCl, dried over MgSO₄, filtered and concentrated to give 0.8 g (84%) of a white solid which was characterized by the loss of the NMR absorption at 3.7 ppm.

Condensation with AsP(OtBu)OH:

Asp(OtBu)OH (2.51 g) was dissolved in 40 mL of dry DMF under argon and 8.2 mL of bis(trimethylsilyl) acetamide (BSA) and the reaction was allowed to stir 40 minutes. In a separate flask, Mu-Val-Ala-OH (4.0 g) was dissolved in 200 mL of dry THF under argon and the resulting solution was cooled to −15° C. and one equivalent of N-methylmorpholine was added followed by one equivalent of isobutylchloroformate and the resulting mixture was allowed to stir 20 minutes and then the first reaction was then poured into the second reaction and both were maintained at −15° C. for one hour and then allowed to come slowly to room temperature and to stir overnight. The reaction was poured into 150 mL of 1N HCl and extracted with 2×200 mL of ethyl acetate. The combined organic fractions were washed with 15 mL 1N HCl, brine (50 mL), dried over MgSO₄ (with decolorizing carbon), filtered, and the solvents were removed under reduced pressure to yield 4.89 g of Mu-Val-Ala-Asp(OtBu)OH.

Conversion to the diazoketone:

Mu-Val-Ala-Asp(OtBu)OH (4.89 g) was dissolved in 250 mL of freshly distilled THF under argon and the resulting solution was cooled to −15° C. Next one equivalent of N-methyl morpholine followed by one equivalent of isobutyl chloroformate was added. The reaction was allowed to activate at this temperature for 20 minutes and then poured through a filter into a solution of diazomethane in ether that was made from 10.8 of diazald according to the supplier's (Aldrich) directions. The reaction was allowed to come slowly to room temperature and to stir overnight. The next day the reaction was washed with water, bicarbonate and brine (50 mL each), dried over MgSO₄, filtered and the solvents were removed under reduced pressure to give a yellow oil showing five spots on TLC (silica gel, CHCl₃/isopropanol:97/3). The lowest $R_f$ is isolated by chromatography on 300 g of silica gel and is shown to be the product by the CHN₂ absorption in the NMR at δ 5.75.

Conversion to the bromoketone:

Mu-Val-Ala-Asp(OtBu)CHN2 was dissolved in 45 mL of methylene chloride and the resulting solution was cooled to −15° C. Next 1.7 ml of 30% methylene chloride dissolved in 30 ml methylene chloride was added dropwise and the reaction was monitored by TLC (silica gel, CHCl₃/isopropanol). The reaction was then poured into brine and the organic fraction was washed with sodium bicarbonate (aq), brine, and dried over MgSO₄, filtered, and the solvents were removed under reduced pressure to give a crude gold solid which was purified by dissolving the material in a minimum of methylene chloride and precipitation in ether/hexane. The product Mu-Val-Ala-Asp(OtBu)CH₂Br is characterized in the NMR (100 MHz, CDCl₃) by the disappearance of the diazoketone absorbance at δ 5.75 and the appearance of a singlet at δ 4.18.

ICE Inhibitors:

Mu-Val-Ala-Asp(OtBu)CH₂Br (0.36 mmol), potassium fluoride (1.09 mmol) and the hydroxy heterocycle (0.546 mmol) was sealed under argon and then 8 mL of dry DMF was added and the reaction was allowed to stir overnight. The next day the reagents were removed either by dilution with ethyl acetate and washing brine or by passage through silica gel. The solvents were removed under vacuum and the product was isolated by size exclusion chromatography (LH20). In this manner the following compounds were prepared:

N-Morpholinecarbonyl-L-Valyl-L-Alanyl-Aspartyl (OtBu)-α-(ascorbityl) methylketone (mp. 138–144° C.); N-Morpholinecarbonyl-L-Valyl-L-Alanyl-Aspartyl(OtBu)-α-(-4-oxy-(3-azo-m-anisidine) methyl ketone: NMR (CDCl₃) δ 0.95 (dd, 6H, Val Ch₃), 1.4 (s, 12H, OtBu+Ala CH₃), 2.1 (m, 1H, Val CH), 2.9 (d, 2H, CH₂ sidechain), 3.3 (t, 4H, MU), 3.7 (t, 4H, MU), 3.85 (s, 3H, OCH₃, 4.2 (t, 1H), 4.6 (t, 1H), 4.7 (d, 2H), 4.9 (m, 3H, CH₂O), 6.9 (d, 1H), 7.1 (m, 4H) 7.9 (d, 1H).

Removal of the tBu in the above inhibitors was effected with 25% trichloroacetic acid in methylene chloride to give the corresponding free acid inhibitors.

EXAMPLE 11

Synthesis of Calpain Inhibitors

The following example is meant to be illustrative of a calpain inhibitor but is not meant to be restrictive as numerous variations in peptide and leaving groups of this invention can be envisioned without undue experimentation.

Acetyl-Leucyl-Leucyl-Phenylalanyl-α-(-4-oxy-dihydrofuran-2-one) methyl ketone

Ac-Leu-Leu-OCH₃:

Acetyl-Leucine (5.0 g) was dissolved in 150 mL of distilled THF under argon and the resulting solution was cooled to −15°. Next one equivalent of N-methyl morpholine followed by one equivalent of isobutyl chloroformate was added and the reaction was allowed to activate 20 minutes and then another equivalent of N-methyl morpholine followed by HCl-LeuOMe (5.25 g). The reaction is allowed to slowly come to room temperature and stir overnight. The reaction was then poured into 150 mL of 1N HCl and extracted with ethyl acetate (2×150 mL). The combined organic fractions were washed with 1N HCl (15 mL), brine (50 mL), and dried over MgSO₄, filtered and the solvent was removed under reduced pressure and then high vacuum. TLC (silica gel, CHCl₃/isopropanol:95:5) showed the product Ac-Leu-Leu-OCH₃ to be a single spot $R_f$ 0.36. NMR (100 MHz) δ 0.95 (d, 12H), 1.5 (bs, 6H), 2.0 (s, 3H), 3.7 (s, 3H), 4.5 (q, 2H), 6.6 (d, 1H), 6.8 (d, 1H).

Hydrolysis to the Free Acid:

Ac-Leu-Leu-OCH₃ (7.8 g) was dissolved in 150 mL of methanol and then 38 mL of 1N sodium hydroxide was added and the reaction was allowed to stir at room temperature for about 4 hours. The methanol was removed under reduced pressure and an additional 10 mL of 1N sodium hydroxide was added and the water fraction was extracted with 10 mL of ethyl acetate. The water fraction was then neutralized with 1N HCl and extracted with ethyl acetate (3×50 mL). The combined organic fraction was washed with brine and dried over MgSO₄, filtered and the solvent was removed under reduced pressure. δ 0.95 (d, 12H), 1.5 (br s, 6H), 2.0 (s, 3H), 4.5 (q, 2H), 6.6 (d, 1H), 6.8 (D, 1H), 9.5 (bs, 1H).

Condensation with PheOMe.

Ac-Leu-Leu-OH was dissolved in 200 mL of distilled THF under argon and the solution was cooled to −15° C.

Next one equivalent of N-methyl morpholine followed by one equivalent of isobutyl chloroformate was added and the reaction was allowed to activate for 20 minutes. An additional equivalent of N-methyl morpholine followed by HCl-HPheOCH$_3$ was added and the reaction was allowed to come slowly to room temperature and stir overnight. The reaction was poured into 200 mL of 1N HCl and extracted with ethyl acetate (2×150 mL). The organic fraction was washed with 1N HCl (20 mL), brine (50 mL), and dried over MgSO$_4$, filtered and the solvents removed under reduced pressure and then high vacuum to leave a solid white cake (TLC, silica gel, CHCl$_3$/isopropanol R$_f$ 0.35). NMR (100 MHz) δ 0.95 (d, 12H), 1.6 (bs, 6H), 2.1 (s, 3H), 3.1 (d, 2H), 3.6 (s, 3H), 4.7 (m, 3H), 6.9 (d, 1H), 7.2 (m, 5H), 7.5 (d, 1H).

Conversion to the Free Acid.

Ac-Leu-Leu-Phe-OMe was dissolved in 150 mL of methanol and 26 mL of 1N sodium hydroxide was added and the rection was stirred 4 hours at which time the methanol was removed under reduced pressure and an additional 7 mL of sodium hydroxide was added. This water fraction was then washed with ethyl acetate (10 mL) and neutralized by the addition of 1N HCL. The resulting mixture was extracted with ethyl acetate 2×100 mL and the extract washed with 1N HCL, brine and dried over MgSO$_4$, filtered and the solvents were removed under reduced pressure to give 7.56 g (94%) of Ac-Leu-Leu-Phe-OH as a white solid. The NMR (100 MHz, CDCl$_3$) of the product acid bears striking resemblance to that of the precursor ester except for the loss of a signal at δ 3.6 and the appearance of a broad singlet at 10.1 (1H).

Conversion to the Diazoketone:

Ac-Leu-Leu-Phe-OH (4.68 g) was dissolved in 200 mL of freshly distilled THF and a methanol-ice bath was applied. Next one equivalent of N-methyl morpholine followed by one equivalent of isobutyl chloroformate was added and the reaction was allowed to activate for 20 minutes and then the resulting mixture was poured through filter paper into diazomethane/ether made from 10.8 g if Diazald according to the supplier's (Aldrich) directions. The reaction was allowed to come slowly to room temperature and to stand overnight. The reaction was washed with water (2×50 ml), sodium bicarbonate (50 mL), brine (50 mL), and then dried over MgSO$_4$, filtered and the solvents were removed under reduced pressure to give after column chromatography (silica gel, CHCl$_3$/isopropanol:93/7) 3.07 g (61%) of a yellow powder. NMR (100 MHz, CDCl$_3$) δ 0.95 (d, 12H), 1.6 (bs, 6H), 2.1 (s, 3H), 3.1 (d, 2H), 4.7 (m, 3H), 5.6 (s, 1H), 6.9 (d, 1H), 7.2 (m, 5H), 7.5 (d, 1H).

Conversion to the Bromide.

Ac-Leu-Leu-Phe-CHN$_2$ (1 g) was dissolved in 175 mL of methylene chloride and then 1.2 mL of 30% HBr/acetic acid that had been diluted with 25 mL methylene chloride was added dropwise at −15° C. As the reaction proceeds bubbles evolve with the formation of a precipitate. The reaction was monitored by TLC (silica gel/CHCl$_3$-isopropanol: 9/1; R$_f$ product 0.54). Upon completion, the rection was poured into 150 mL of brine and the reaction flask was washed with another 150 mL of methylene chloride to dissolve the residual precipitate. The combined organic layers were washed with sodium bicarbonate (aq, 50 mL), brine (50 mL), dried over MgSO$_4$ and concentrated to give a dull white solid. This solid was purified by precipitate from methylene chloride into ether to yield 610 mg (54%) of a white solid TLC (silica gel, CHCl$_3$/isopropanol:9:1) one spot R$_f$ 0.54. NMR (DMSO-d$_6$) δ 0.81 (d, 12H), 1.3 (m, 6H), 1.8 (s, 3H), 3.1 (d, 2H), 4.1 (m, 2H), 4.3 (s, 2H), 4.6 (q, 1H), 7.2 (m, 5H), 8.0 (d, 2H), 8.4 (d, 1H).

Calpain inhibitor:

Ac-Leu-Leu-Phe-CH$_2$Br (200 mg), tetronic acid (65 mg) and potassium fluoride (68 mg) were mixed under argon with 5 mL of dry DMF overnight. The reaction was then diluted with 20 mL of ethyl acetate and the reaction was washed with 10 mL sodium bicarbonate (aq), brine (10 mL), and dried over MgSO$_4$. The reaction was filtered and the solvents were removed under reduced pressure and then high vacuum to give 107 mg (49%) of acetyl-leucyl-leucyl-phenylalanyl-α-(4-oxy-dihydrofuran-2-one)methyl ketone.

EXAMPLE 12

Synthesis of Other Heterocyclic Inhibitors

Using the following procedures other heterocyclic cathepsin inhibitors are prepared.

N-Morpholinecarbonyl-L-phenylalanyl-L-homophenylalanine-α-(4-oxy-N-acetyl-proline methyl ester) methyl ketone (A1)

MuPheHPheCH$_2$Br (250 mg), N-acetyl-proline methyl ester (2.0 g), potassium fluoride (232 mg), and potassium carbonate (276 mg) are placed under argon and then 1.5 mL of dry DMF was added and the reaction was allowed to stir at room temperature for 100 minutes. The reaction was then passed through a short silica gel column (ethyl acetate) and the solvents were removed in vacuo. Precipitation in ether produced a white solid, mp. 81–84° C.

N-Morpholinecarbonyl-L-phenylalanyl-L-homophenylalanyl-α-(3-oxy-5-ethyl-4-methyl 2(5H) furanone) methyl ketone (A2)

MuPheHPheCH$_2$Br (100 mg), potassium fluoride (45 mg), and 5-ethyl-3-hydroxy-4-methyl-2(5H) furanone (110 mg) was placed under argon in 5 mL of dry DMF and the reaction was stirred at room temperature overnight. The next day the reaction was diluted with ethyl acetate and washed with aqueous sodium bicarbonate and the brine, dried over MgSO$_4$, filtered and the solvents were removed in vacuo. The product was purified by size exclusion chromatography (LH-20, methanol) to give a white solid, mp. 65–71° C.

N-Morpholinecarbonyl-L-phenylalanyl-L-homophenylalanine-α-(8-oxy-quinoline) methyl ketone (A3)

To MuPheHPheCH$_2$Br (100 mg), potassium fluoride (45 mg) and 8-hydroxyquinoline (123 mg) in a test tube under argon was added 5 mL of dry DMF and the reaction was allowed to stir for four hours. The reaction was then passed through a short silica gel column and the solvents were removed in vacuo. The product was purified by first size exclusion chromatography (LH-20, methanol) and then by crystallization from methylene chloride/ether to give 65 mg of crystals. The product was characterized by NMR (100 MHz) δ 8.5–8.0 (m, hetero aromatic), 7.5–6.5 (mm, homo and heteroaromatic), 3.75–3.5, 3.25–3.0 (2m, Mu H), 2.75 (s, heteroaromatic Me) ppm.

N-Morpholinecarbonyl-L-phenylalanyl-L-homophenylalanine-α-(2-oxy-4-methyl-quinoline) methyl ketone (A4)

MuPheHPheCH$_2$Br (100 mg), potassium fluoride (45 mg), and 2-hydroxy-4-methyl-quinoline (123 mg) was placed in a test tube under argon and 5 mL of dry DMF was added. The reaction was allowed to stir at room temperature overnight. The reaction was then passed through a short silica gel plug and the solvents were removed in vacuo. The residue was purified first by size exclusion chromatography and then by precipitation into ether to give a solid, mp. 180–183° C.

N-Morpholinecarbonyl-L-phenylalanyl-L-homophenylalanine-α-(4-oxy-quinoline) methyl ketone (A5)

MuPheHPheCH$_2$Br (100 mg), potassium fluoride (45 mg), and 4-hydroxyquinoline was placed in a test tube under argon and 5 mL of dry DMF was added. The reaction was stirred for 3.5 hours and then passed through a short silica gel column (ethyl acetate). The solvents were removed in vacuo and the residue was purified by size exclusion chromatography followed by precipitation of the collected product in ether to yield a white powder, mp. 107–111° C.

N-Morpholinecarbonyl-L-phenylalanyl-L-homophenylalanine-α-(4-oxy-quinazoline) methyl ketone (A6)

MuPheHPheCH$_2$Br (100 mg), 5-methyl-5-triazolo[1,5a]-pyrimidin-7-ol (116 mg), and potassium fluoride (45 mg) was added together under argon in a dry test tube and 5 mL of dry DMF was added. The reaction was stirred at room temperature for 3.5 hours and then the reaction was diluted with ethyl acetate and passed through a plug of silica gel. The solvents were removed in vacuo and the product was purified by size exclusion chromatography (LH-20, methanol) to give a solid product, mp. 129–132° C.

N-Morpholinecarbonyl-L-phenylalanyl-L-homophenylalanine-α-(2-oxy-benzimidazole) methyl ketone (A7)

MuPheHPheCH$_2$Br (100 mg), 2-hydroxybenzimidazole (104 mg), and potassium fluoride (45 mg) was added together under argon in a dry test tube and 5 mL of dry DMF was added. The reaction was stirred at room temperature for 3 hours and then the reaction was diluted with ethyl acetate and passed through a plug of silica gel. The solvents were removed in vacuo and the product was purified by size exclusion chromatography (LH-20, methanol) to give an off white solid product, mp. 115–120° C.

N-Morpholinecarbonyl-L-phenylalanyl-L-homophenylalanine-α-(1-oxy-isoquinoline) methyl ketone (A8)

MuPheHPheCH$_2$Br (100 mg), potassium fluoride (45 mg), isocarbostyril (112 mg), are placed under argon and then 4 mL of dry DMF is added. The reaction is stirred at room temperature for three hours and then the reaction is diluted with ethyl acetate and passed through a short silica gel column. The solvents are removed in vacuo and the product purified by size exclusion chromatography (LH-20, methanol) to give a white solid, mp. 104–107° C.

N-Morpholinecarbonyl-L-phenylalanyl-L-homophenylalanine-α-(7-oxy-coumarin) methyl ketone (A10)

MuPheHPheCH$_2$Br (200 mg) and potassium fluoride (90 mg) was added under argon to 1.5 mL of DMF and 250 mg of 7-hydroxycoumarin was added. The reaction turns a bright gold and is allowed to stir for one hour at which time TLC shows total loss of bromide. The reaction was then passed through a short column of silica gel (CHCl$_3$/isopropanol, 9:1) and the solvents were removed in vacuo. Further chromatography (LH-20/methanol) gave after removal of solvent a white solid foam, mp. 87–89° C.

In a like manner N-Morpholinecarbonyl-L-phenylalanyl-L-homophenylalanyl-α-(7-oxy-4-methyl-coumarin) methyl ketone (A9) was prepared, mp. 99–102° C.

N-Morpholinecarbonyl-L-phenylalanyl-L-homophenylalanine-α-(2-oxy-benzofuran) methyl ketone (A11)

MuPheHPheCH$_2$Br (100 mg), 2-coumaranone (52 mg) and potassium fluoride (45 mg) were placed in a test tube under argon and then one mL of DMF was added and the reaction turns a cherry red. The reaction after 20 minutes shows a loss of starting bromide (TLC, Silica gel, CHCl$_3$/isopropanol:9/1) R$_f$ product, 0.59; R$_f$ bromide 0.48. The reaction was passed through a short plug of silica gel (ethyl acetate) and the solvents were removed in vacuo. The residue was dissolved in a minimum of methylene chloride and precipitated in ether and the precipitate filtered to yield a white solid, mp. 94–110° C.

N-Morpholinecarbonyl-L-phenylalanyl-L-homophenylalanine-α-(3-oxy-2-methyl-4-pyrone) methyl ketone (A12)

MuPheHPheCH$_2$Br (94 mg), potassium fluoride (45 mg), and 3-hydroxy-2-methyl-4-pyrone was placed in a test tube under argon and 5 mL of dry DMF was added and the reaction was stirred at room temperature for two hours at which time the reaction showed a loss of starting material (silica gel, CHCl$_3$/isopropanol, 9/1). The reaction was then passed through a short plug of silica gel and the solvents were removed in vacuo. The product was then purified by size exclusion chromatography to give after evaporation of solvent a gold solid, mp. 71–81.

N-Morpholinecarbonyl-L-phenylalanyl-L-homophenylalanine-α-(2-oxy-benzothiazole) methyl ketone (A13)

MuPheHPheCH$_2$Br (100 mg), 2-hydroxybenzothiazole (117 mg), and potassium fluoride (45 mg) were placed in a test tube under argon and 3 mL of dry DMF was added. The reaction was stirred at room temperature until TLC (silica gel) showed loss of starting material. The reaction was passed through a short silica gel column, the solvents were removed in vacuo. The residue is dissolved in hot methanol and a white precipitate forms which upon filtration proves to be the product, mp. 211–213° C.

N-Morpholinecarbonyl-L-phenylalanyl-L-homophenylalanine-α-(2-oxy-thiophene) methyl ketone (A14)

MuPheHPheCH$_2$Br (265 mg), potassium carbonate (119 mg), and potassium fluoride (284 mg) were added together under argon and then one gram of thiophenone in 4 mL DMF was added and the reaction was allowed to stir at room temperature for 2 hours. The solvents were removed in vacuo and the products were separated on a 10 g silica gel column.

N-Morpholinecarbonyl-L-phenylalanyl-L-homophenylalanine-α-(5-oxy-3-methyl-4-isoxazolecarboxylate) methyl ketone (A15)

MuPheHPheCH$_2$Br (510 mg), ethyl 5-hydroxy-3-methyl-4-isoxazole carboxylate sodium salt, and 5 mL of DMF was allowed to stir under argon at room temperature for 4 hours. The reaction was then passed through a short plug of silica gel (CHCl₃/isopropanol) and the solvents were removed in vacuo. The product was purified by size exclusion chromatography (LH-20) to give after precipitation in ether and filtration a white solid that melted with a phase change at 98–105 and then again at 125–131° C.

Formation of Alkyl Halide Salts from Inhibitors Containing Nitrogen in the Heterocycle Leaving Group: The methyl iodide isoquinoline salt of N-Morpholinecarbonyl-L-phenylalanyl-L-homophenylalanine-α-(1-oxy-isoquinoline) methyl ketone (A16)

Compound A8 (83 mg) is dissolved in 2 mL of toluene and one mL of iodomethane is added. The reaction is sealed and allowed to stir for two days. A white precipitate forms which is filtered and dried under vacuum to give a white solid, mp. 159–161° C.

CONSTUCTIONS OF INHIBITORS WITH OTHER HETEROCYCLES
(IC$_{50}$ Cathepsin B Inhibition)

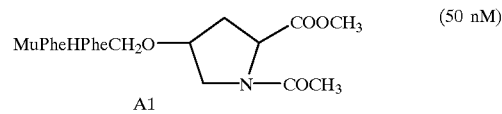
A1 (50 nM)

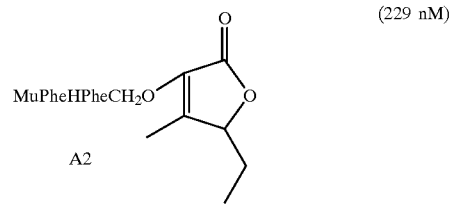
A2 (229 nM)

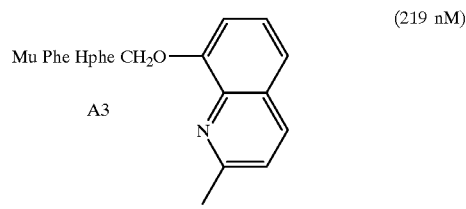
A3 (219 nM)

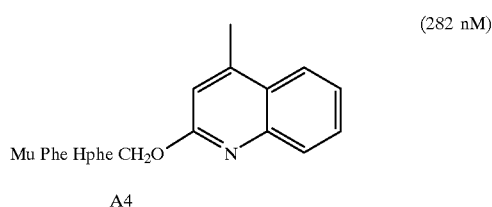
A4 (282 nM)

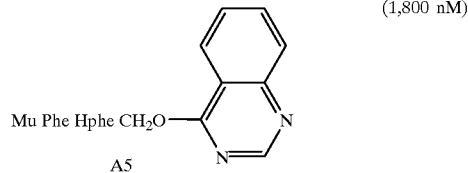
A5 (1,800 nM)

-continued

CONSTUCTIONS OF INHIBITORS WITH OTHER HETEROCYCLES
(IC$_{50}$ Cathepsin B Inhibition)

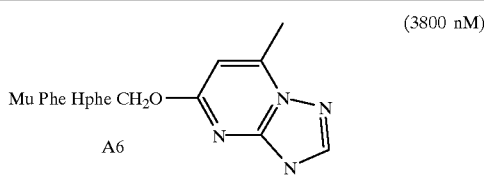
A6 (3800 nM)

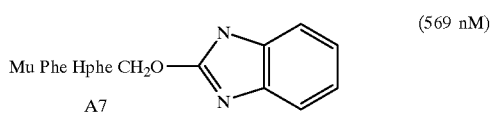
A7 (569 nM)

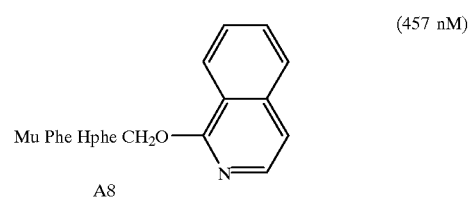
A8 (457 nM)

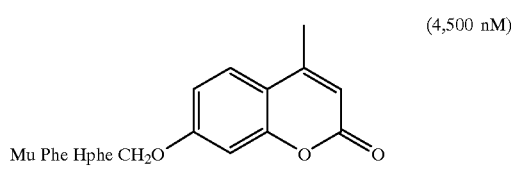
A9 (4,500 nM)

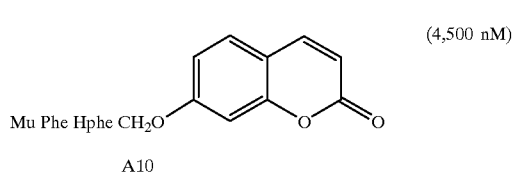
A10 (4,500 nM)

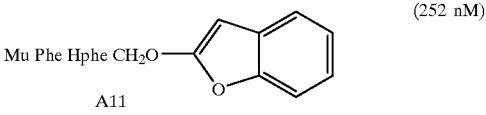
A11 (252 nM)

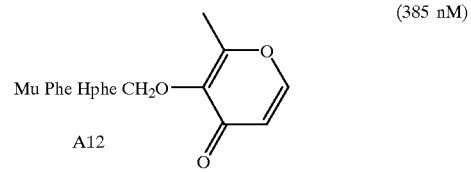
A12 (385 nM)

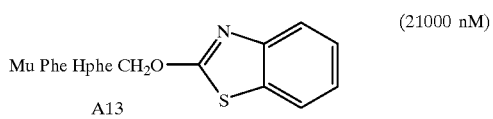
A13 (21000 nM)

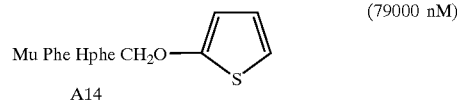
A14 (79000 nM)

-continued

CONSTUCTIONS OF INHIBITORS WITH OTHER HETEROCYCLES
(IC$_{50}$ Cathepsin B Inhibition)

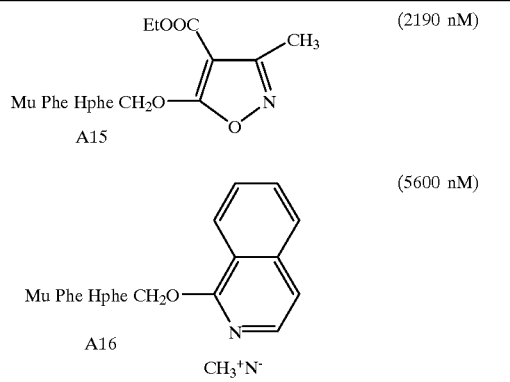

EXAMPLE 13

Synthesis of Inhibitors With Heterocycles in their Peptide Backbones

The reaction scheme shown below is a first method for the synthesis of cysteine protease inhibitors with heterocycles in their peptide backbones. The synthetic method is an adaptation from that of Amos B. Smith and Ralph Hirshman as disclosed in "Design and Synthesis of Peptidomimetic Inhibitors of HIV-1 Protease and Renin," 37 *J. Med. Chem.* 215.

The hydrolysis of this ester to the acid makes a equivalent to N-(morpholine carbonyl) phenyl alanine homophenylalanine that may substitute in the synthesis of the inhibitors of this invention.

The reaction schemes shown below illustrate a second method for the synthesis of cysteine protease inhibitors with heterocycles in their peptide backbones. This synthetic method is an adaptation from that of Damewood et al., "Nonpeptidic Inhibitors of Human Leukocyte Elastase," 37 *J. Med. Chem.* 3303.

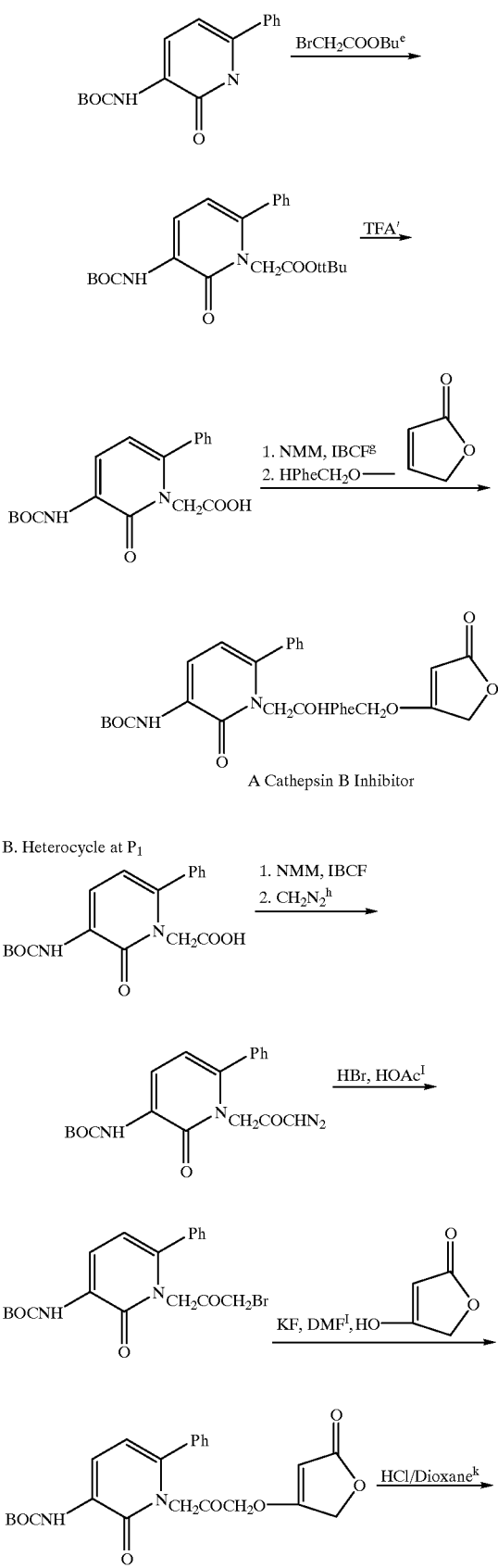

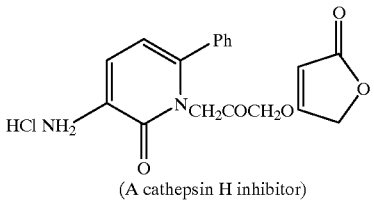

(A cathepsin H inhibitor)

Reagents: (a) sodium ethoxide/ether; (b) cyanoacetamide, piperidine acetate, water; (c) 48% HBr, acetic acid (d) diphenyl phosphoryl azide (Aldrich), triethyl amine, then benzyl alcohol; (e) sodium hydride, DMF, then tert- butyl bromoacetate, (f) trifluoroacetic acid in methylene chloride; (g) N-methyl morpholine, isobutyl chloroformate then an unblocked amino acid alpha oxy-heterocycle methyl ketone such as L-homophenyl-alpha-4-oxy-dihdro-furan-2-one) methyl ketone (example 9); (h) N-methyl morpholine, isobutyl chloroformate, then diazomethane/ether from Diazald (Aldrich); 30% HBr/acetic acid in methylene chloride; (j) potassium fluoride, DMF, oxyheterocycle such as tetronic acid; (k) hydrochloric acid in dioxane. Note that this one amine acid fragment can be condensed as above with another blocked amino acid fragment (B-P$_2$) to produce a cathepsin B, L type inhibitor.

EXAMPLE 14

Protocol for Testing ICE Inhibitors

The percent inhibition of two inhibitors, N-Benzoxycarbonyl-Valyl-Alanyl-Aspartyl-α-(4-oxy-(6-methyl-2-pyrone) methyl ketone, and N-Morpholinecarbonyl-L-Valyl-L-Alanyl-Aspartyl (OtBu)-α-(ascorbityl) methyl ketone, on IL-1β protease was determined as follows. A 10 mM dithiothreitol, 100 mM Hepes, 10% sucrose, 0.1% CHAPS, pH 7.5 buffer solution with 50 $\mu$M Z-YVAD-AFC substrate was prepared. The enzyme was activated for 1 minute in the buffer/substrate solution at room temperature. Inhibitor was prepared as stock solution in dimethyl sulfoxide. Inhibitor and enzyme/buffer were incubated for 15 minutes at 37C. Final concentrations of inhibitor were 2000 nM, 200 nM, and 20 nM. Enzyme activity was followed by the release of free fluorescent detecting group over sixty minutes at 37C, as compared to the control.

EXAMPLE 15

Protocol for Testing Calpain Inhibitors

The percent inhibition of one inhibitor, Acetyl-Leucyl-Leucyl-Phenylalanyl-α-(4-oxy-dihydrofuran-2-one) methyl ketone, on calpain (Calcium Activated Neutral Protease) was determined as follows. A 50 mM Hepes, 10 mM calcium chloride, 5 mM cysteine, 1 mM β-mercaptoethanol, pH 7.5 buffer solution was prepared. The enzyme was activated for 1 minute in the buffer solution at room temperature. Inhibitor was prepared as stock solution in dimethylformamide. Inhibitor and enzyme/buffer were incubated for 30 minutes at 37° C. Final concentrations of inhibitor were 20 $\mu$M, 2 $\mu$M, and 200 nM. Enzyme activity was followed with 200 $\mu$M Boc-Valynyl-Leucyl-Lysine-AFC substrate by the release of free fluorescent detecting group over minutes at 37° C., as compared to the control. The inhibitor showed activity against the enzyme at less than 2 $\mu$M.

While the invention has been illustrated and described in detail in the drawing and foregoing description, the same is to be considered as illustrative and not restrictive in character, it being understood that only the preferred embodiment has been shown and described and that all changes and modifications that come within the spirit of the invention are desired to be protected.

What is claimed is:

1. Cathepsin or calpain inhibitors of the formula:

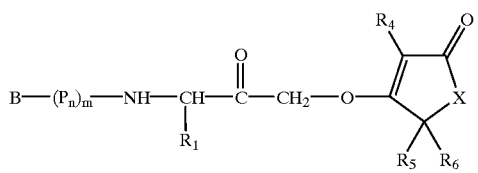

where

B is H or an N-terminal blocking group;

$R_1$ is an amino acid side chain of an amino acid other than Asp;

each $P_n$ is an amino acid residue, or is a heterocyclic replacement of the amino acid;

m is 0 or a positive integer;

$R_4$ is a hydroxyl, alkoxyl, acyl, hydrogen, alkyl or phenyl;

$R_5$ and $R_6$ are jointly a carboxyl group or a double bond terminating in an alkyl or an aryl group, or are independently acyl, aryl or heteroaryl if $R_4$ is hydrogen, alkyl or phenyl, or are independently acyl, alkyl, hydrogen, aryl or heteroaryl otherwise; and X is N, S, O or $CH_2$.

2. Cathepsin or calpain inhibitors according to claim 1 wherein X is O.

3. Protease inhibitors of the formula:

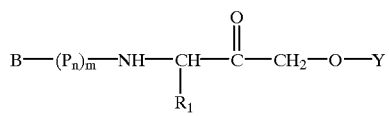

where

B is H or an N-terminal blocking group;

each $P_n$ is an amino acid residue, or is a heterocyclic replacement of the amino acid;

$R_1$ is an amino acid side chain of an amino acid other than Asp, or is a heterocyclic replacement thereof;

m is 0 or a positive integer;

Y is a heterocyclic leaving group of not more than three heteroatoms per ring in which the peptidyl α-oxy-portion is bonded to a carbon of the heterocycle.

4. A protease inhibitor according to claim 3 wherein Y is a leaving group of the formula:

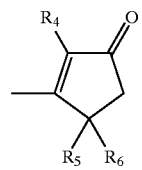

where $R_4$ is a hydroxyl, alkoxyl, acyl, hydrogen, alkyl or phenyl;

$R_5$ and $R_6$ are jointly a carboxyl group or a double bond terminating in an alkyl or an aryl group, or are independently acyl, aryl or heteroaryl if $R_4$ is hydrogen, alkyl or phenyl, or are independently acyl, alkyl, hydrogen, aryl or heteroaryl otherwise; and X is N, S, O or $CH_2$.

* * * * *